US008053462B2

(12) United States Patent
Somei et al.

(10) Patent No.: US 8,053,462 B2
(45) Date of Patent: Nov. 8, 2011

(54) INDOLE DERIVATIVE AND APPLICATION THEREOF

(76) Inventors: Masanori Somei, Ishikawa (JP); Atsuhiko Hattori, Chiba (JP); Nobuo Suzuki, Toyama (JP)

( * ) Notice: Subject to any disclaimer, the term of this patent is extended or adjusted under 35 U.S.C. 154(b) by 445 days.

(21) Appl. No.: 10/591,899

(22) PCT Filed: Mar. 4, 2005

(86) PCT No.: PCT/JP2005/003743

§ 371 (c)(1),
(2), (4) Date: Sep. 7, 2006

(87) PCT Pub. No.: WO2005/084664

PCT Pub. Date: Sep. 15, 2005

(65) Prior Publication Data

US 2007/0197629 A1 Aug. 23, 2007

(30) Foreign Application Priority Data

Mar. 8, 2004 (JP) ................................ 2004-064408

(51) Int. Cl.
*A01N 43/38* (2006.01)
*A61K 31/405* (2006.01)
*C07D 209/16* (2006.01)

(52) U.S. Cl. ....................................... 514/415; 548/504

(58) Field of Classification Search ........................ None
See application file for complete search history.

(56) References Cited

U.S. PATENT DOCUMENTS

| | | | | |
|---|---|---|---|---|
| 4,087,444 | A | 5/1978 | Flaugh et al. | |
| 4,614,807 | A | 9/1986 | Flaugh | |
| 5,272,141 | A | 12/1993 | Fraschini et al. | |
| 5,276,051 | A | 1/1994 | Lesieur et al. | |
| 5,308,866 | A | 5/1994 | Lesieur et al. | |
| 5,380,750 | A | 1/1995 | Lesieur et al. | |
| 5,430,029 | A | 7/1995 | Biella et al. | |
| 5,552,428 | A | 9/1996 | Fraschini et al. | |
| 5,763,471 | A * | 6/1998 | Fourtillan et al. | 514/409 |
| 6,552,064 | B2 * | 4/2003 | Attala | 514/415 |

FOREIGN PATENT DOCUMENTS

| | | | |
|---|---|---|---|
| JP | 52-57169 | A | 5/1977 |
| JP | 5-155769 | A | 6/1993 |
| JP | 6-183968 | A | 7/1994 |
| JP | 6-199784 | A | 7/1994 |
| JP | 6-263635 | A | 9/1994 |

OTHER PUBLICATIONS

Naguib et al. The hypnotic and analgesic effects of 2-bromomelatonin. Anesth Analg, 2003, 97: 763-8.*

Tarzia et al. 1-(2-alkanamidoethyl)-6-methoxyindole derivatives: a new class of potent indole melatonin analogues. J. Med. Chem., 40 (13), 2003-2010, 1997.*

Edited by Osol. Remington's Pharmaceutical Sciences. 1980, pp. 420-425.*

Faust et al. Mapping the melatonin receptor. 6. melatonin agonists and antagonists derived from 6-isoindolo[2,1-a]indoles, 5,6-dihydroindolo[2,1-a]isoquinolines, and 6,7-dihydro-5H-benzo[c]azepino[2,1-a]indoles. J. Med. chem, 2000, 43, 1050-1061.*

Somei et al. Synthesis of melatonin and its derivatives. Heterocycles, vol. 53, No. 8, 2000, pp. 1725-1736.4-5 and 13-15.*

Schafer et al. Failure is an option: learning from unsuccessful proof-of-concept trials. Drug Discovery Today 2008, 13 (21/22), 913-916.*

Horig et al. Review: From bench to clinic and back: Perspective on the 1st IQPC Translational Research Conference. Journal of Translational Medicine 2004, 2(44).*

J. G. Cannon Chapter Nineteen in Burger's Medicinal Chemistry and Drug Discovery, Fifth Edition, vol. I: Principles and Practice, Wiley-Interscience 1995, pp. 783-802, 784.*

Patani et al. (Chem. Rev., 1996, 96, 3146-76).*

Masanori Somei et al.; Syntheses of Melatonin and Its Derivatives; Heterocycles, vol. 53, No. 8, 2000, pp. 1725-1736.

Nobuo Suzuki et al.; Melatonin suppresses osteoclastic and osteoblastic activities in the scales of goldfish; Journal of Pineal Research; 2002; 33; pp. 253-258.

Roth J. A. et al., J. Biol. Chem., vol. 274, No. 31, pp. 22041 to 22047, 1999.

* cited by examiner

*Primary Examiner* — Brandon Fetterolf
*Assistant Examiner* — Anna Pagonakis
(74) *Attorney, Agent, or Firm* — Birch, Stewart, Kolasch & Birch, LLP

(57) ABSTRACT

This invention relates to a compound represented by formula (I) or a salt thereof, and a therapeutic agent for osteoporosis, an osteoblast activator, and an osteoclast suppressor comprising the same:

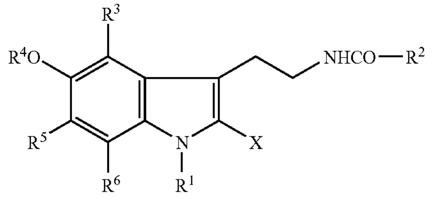

wherein X represents a halogen atom; $R^1$ represents a hydrogen atom, substituted or unsubstituted $C_{1-6}$ alkyl, substituted or unsubstituted $C_{2-6}$ alkenyl, substituted or unsubstituted $C_{2-6}$ alkynyl, a substituted or unsubstituted aromatic group, substituted or unsubstituted aralkyl, substituted or unsubstituted acyl, substituted or unsubstituted arylsulfonyl, substituted or unsubstituted $C_{1-6}$ alkylsulfonyl, or hydroxyl; $R^2$ represents substituted or unsubstituted $C_{1-21}$ alkyl; $R^3$, $R^5$ and $R^6$, which may be the same or different, each represent a hydrogen atom or a halogen atom; and $R^4$ represents a hydrogen atom or substituted or unsubstituted $C_{1-6}$ alkyl.

12 Claims, 4 Drawing Sheets

INDOLE DERIVATIVE AND APPLICATION THEREOF

TECHNICAL FIELD

The present invention relates to an indole derivative and applications thereof. More particularly, the present invention relates to a therapeutic agent for osteoporosis, an osteoblast activator, and an osteoclast suppressor.

BACKGROUND ART

Osteoporosis is developed as a result of an imbalance between functions of osteoblasts, which play a role in osteogenesis, and osteoclasts, which play a role in deossification. Compounds that activate osteoblasts and compounds that suppress osteoclasts are considered to be effective in treating osteoporosis. Compounds having a single function, however, cannot produce satisfactory effects. Estrogen is deduced to activate osteoblasts and to suppress osteoclasts, and it is utilized in treating osteoporosis. Since estrogen also affects cells other than bones, particularly reproductive organs, side effects, such as increased risk of uterine cancer or breast cancer, may become an issue of concern. Also, the Ministry of Health, Labour and Welfare (Japan) issued safety information as of Jan. 29, 2004, to warn of the possibility of an increase in the development of breast cancer or dementia due to the prolonged ingestion of estrogen. Since estrogen has a complicated molecular structure, synthesis thereof is complicated and difficult.

Melatonin (N-acetyl-5-methoxytryptamine), which is an indole derivative represented by formula (I), is reported to act suppressively both on osteoblasts and osteoclasts:

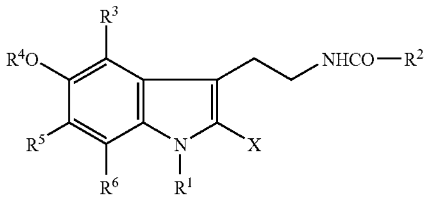

wherein X represents a hydrogen atom; $R^1$ represents a hydrogen atom; $R^2$ represents methyl; $R^3$, $R^5$, and $R^6$ each represent a hydrogen atom; and $R^4$ represents methyl (N. Suzuki and A. Hattori, J. Pineal Res., 33, 253-258, 2002).

Also, it is reported that a compound represented by formula (I) wherein X represents a bromine atom; $R^1$ represents a hydrogen atom; $R^2$ represents methyl; $R^3$, $R^5$, and $R^6$ each represent a hydrogen atom; and $R^4$ represents methyl; a compound represented by formula (I) wherein X and $R^5$ each represent a bromine atom; $R^1$ represents a hydrogen atom; $R^2$ represents methyl; $R^3$ and $R^6$ each represent a hydrogen atom; and $R^4$ represents methyl; a compound represented by formula (I) wherein X and $R^3$ each represent a bromine atom; $R^1$ represents a hydrogen atom; $R^2$ represents methyl; $R^5$ and $R^6$ each represent a hydrogen atom; and $R^4$ represents methyl; and a compound represented by formula (I) wherein X, $R^3$, and $R^5$ each represent a bromine atom; $R^1$ represents a hydrogen atom; $R^2$ represents methyl; $R^6$ represents a hydrogen atom; and $R^4$ represents methyl can be obtained by brominating melatonin, although influences thereof on osteoblasts and osteoclasts have not been examined (M. Somei, Y. Fukui, M. Hasegawa, N. Oshikiri, and T. Hayashi, Heterocycles, 53, 1725-1736, 2000).

DISCLOSURE OF THE INVENTION

The present invention provides an indole derivative that activates osteoblasts and suppresses osteoclasts and a therapeutic agent for osteoporosis, an osteoblast activator, and an osteoclast suppressor using the same.

The present invention includes the following inventions.

(1) A therapeutic agent for osteoporosis comprising a compound represented by formula (I) or a pharmaceutically acceptable salt thereof:

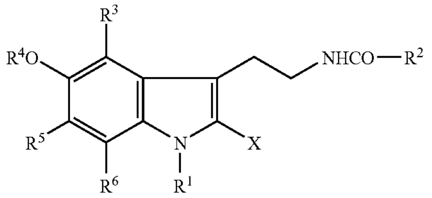

wherein X represents a halogen atom; $R^1$ represents a hydrogen atom, substituted or unsubstituted $C_{1-6}$ alkyl, substituted or unsubstituted $C_{2-6}$ alkenyl, substituted or unsubstituted $C_{2-6}$ alkynyl, a substituted or unsubstituted aromatic group, substituted or unsubstituted aralkyl, substituted or unsubstituted acyl, substituted or unsubstituted arylsulfonyl, substituted or unsubstituted $C_{1-6}$ alkylsulfonyl, or hydroxyl; $R^2$ represents substituted or unsubstituted $C_{1-21}$ alkyl; $R^3$, $R^5$, and $R^6$, which may be the same or different, each represent a hydrogen atom or a halogen atom; and $R^4$ represents a hydrogen atom or substituted or unsubstituted $C_{1-6}$ alkyl.

(2) An osteoblast activator comprising the compound represented by formula (I) defined in (1) or a salt thereof.

(3) An osteoclast suppressor comprising the compound represented by formula (I) defined in (1) or a salt thereof.

(4) A compound represented by formula (I') or a salt thereof:

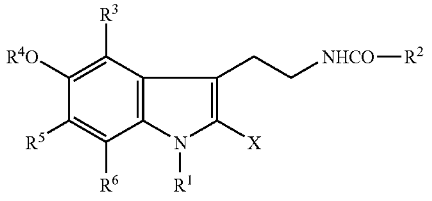

wherein X represents a halogen atom or a hydrogen atom; $R^1$ represents a hydrogen atom, substituted or unsubstituted $C_{1-6}$ alkyl, substituted or unsubstituted $C_{2-6}$ alkenyl, substituted or unsubstituted $C_{2-6}$ alkynyl, a substituted or unsubstituted aromatic group, substituted or unsubstituted aralkyl, substituted or unsubstituted acyl, substituted or unsubstituted arylsulfonyl, substituted or unsubstituted $C_{1-6}$ alkylsulfonyl, or hydroxyl; $R^2$ represents substituted or unsubstituted $C_{1-21}$ alkyl; and $R^3$, $R^5$ and $R^6$, which may be the same or different, each represent a hydrogen atom or a halogen atom, provided that, when X represents a hydrogen atom, at least one of $R^3$, $R^5$ and $R^6$ represents a chlorine atom; and $R^4$ represents a hydrogen atom or substituted or unsubstituted $C_{1-6}$ alkyl (excluding the compound represented by formula (I') wherein X represents a bromine atom; $R^1$ represents a hydrogen atom; $R^2$ represents methyl; $R^3$, $R^5$ and $R^6$ each represent a hydrogen atom; and $R^4$ represents methyl; the compound represented by formula (I') wherein X and $R^5$ each represent a bromine atom; $R^1$ represents a hydrogen atom; $R^2$ represents methyl; $R^3$ and $R^6$ each represent a hydrogen atom; and $R^4$ represents methyl; the compound represented by formula (I') wherein X and $R^3$ each represent a bromine atom; $R^1$ represents a hydrogen atom; $R^2$ represents methyl; $R^5$ and $R^6$ each represent a hydrogen atom; and $R^4$ represents methyl; and the compound represented by formula (I') wherein X, $R^3$, and $R^5$ each represent a bromine atom; $R^1$ represents a hydrogen atom; $R^2$ represents methyl; $R^6$ represents a hydrogen atom; and $R^4$ represents methyl).

(5) The compound represented by formula (I') according to (4) or a salt thereof, wherein X represents a bromine atom; $R^1$ represents substituted or unsubstituted $C_{1-6}$ alkyl, substituted or unsubstituted $C_{2-6}$ alkenyl, substituted or unsubstituted $C_{2-6}$ alkynyl, a substituted or unsubstituted aromatic group, substituted or unsubstituted aralkyl, substituted or unsubstituted acyl, substituted or unsubstituted arylsulfonyl, or substituted or unsubstituted $C_{1-6}$ alkylsulfonyl; $R^2$ represents methyl; $R^3$, $R^5$ and $R^6$, which may be the same or different, each represent a hydrogen atom or a bromine atom; and $R^4$ represents methyl.

(6) A pharmaceutical composition comprising, as an active ingredient, the compound according to (4) or (5) or a pharmaceutically acceptable salt thereof.

EFFECTS OF THE INVENTION

The present invention can provide an indole derivative that activates osteoblasts and suppresses osteoclasts and a therapeutic agent for osteoporosis, an osteoblast activator, and an osteoclast suppressor using the same. The indole derivative of the present invention can be synthesized in an easier manner than estrogen, and it can be mass-produced.

Figure 1A:
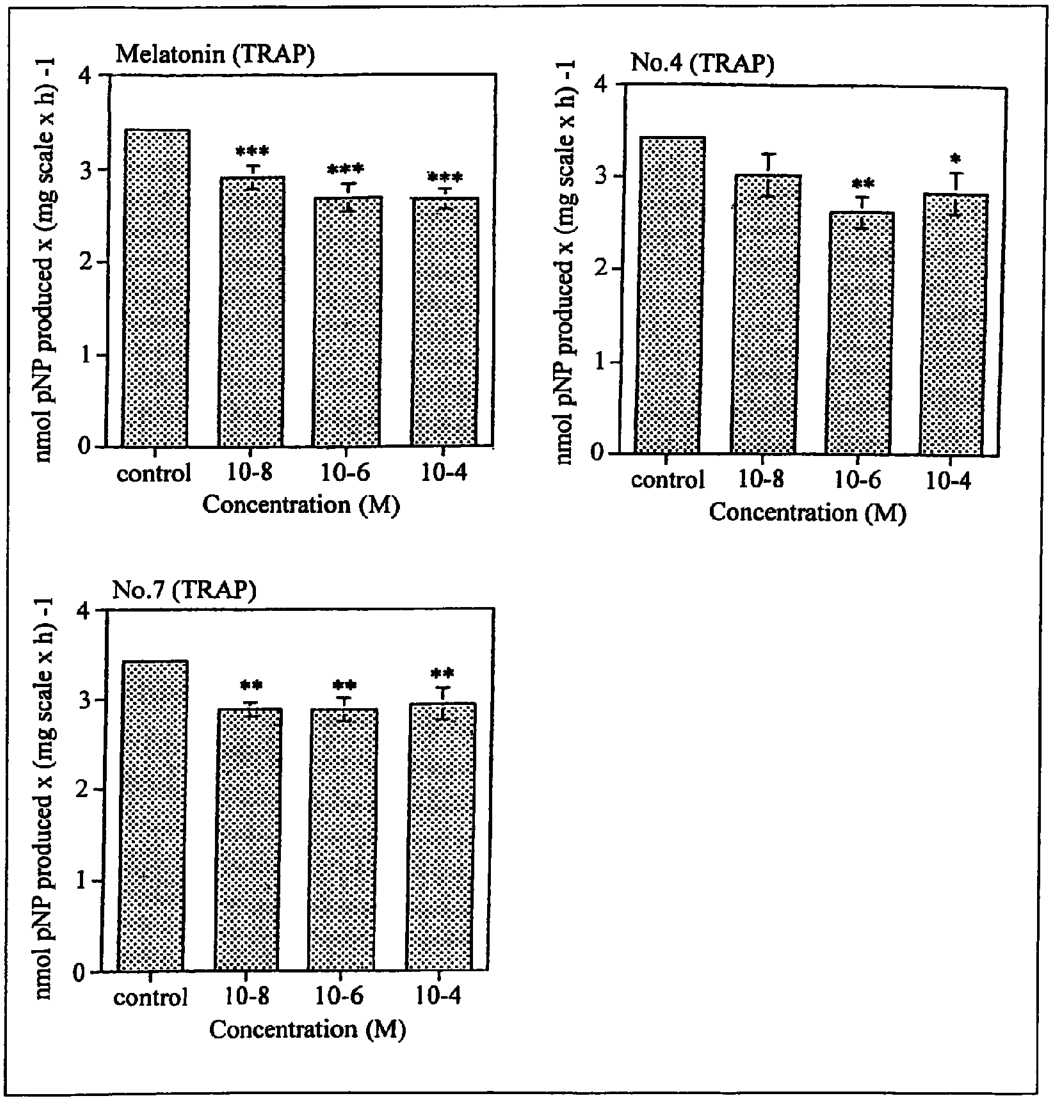
FIG. 1A shows influences of various indole derivatives on osteoclasts.

DESCRIPTION OF SYMBOLS pNP: paranitrophenol
*: $p<0.05$
**: $p<0.01$
***: $p<0.001$
No. 4: 2-Bromomelatonin
No. 7: 2,4,6-Tribromomelatonin (1c) (Example 6)
No. 9: 1-Allyl-2,4,6-tribromomelatonin (Example 2)
No. 10: 2,4,6-Tribromo-1-propargylmelatonin (Example 1)
No. 11: 1-Benzyl-2,4,6-tribromomelatonin (Example 3)
No. 29: 2,4,6,7-Tetrabromomelatonin (1e) (Example 6)

PREFERRED EMBODIMENTS OF THE INVENTION

Hereafter, the present invention is described in detail.

In the present invention, examples of $C_{1-6}$ alkyl and "$C_{1-6}$ alkyl" in each substituent include methyl, ethyl, propyl, isopropyl, butyl, isobutyl, sec-butyl, tert-butyl, pentyl, isopentyl, hexyl, cyclopropyl, cyclobutyl, cyclopentyl, and cyclohexyl.

Examples of $C_{1-21}$ alkyl include methyl, ethyl, propyl, isopropyl, butyl, isobutyl, sec-butyl, tert-butyl, pentyl, isopentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, cyclopropyl, cyclobutyl, cyclopentyl, and cyclohexyl.

In formulae (I) and (I'), $C_{1-21}$ alkyl represented by $R^2$ is preferably $C_{1-6}$ alkyl.

Examples of $C_{2-6}$ alkenyl include vinyl, 1-propenyl, allyl, 1-butenyl, 2-butenyl, pentenyl, and hexenyl.

Examples of $C_{2-6}$ alkynyl include ethynyl, 1-propynyl, 2-propynyl (propargyl), 3-butynyl, pentynyl, and hexynyl.

Examples of aromatic groups include aromatic hydrocarbon groups, such as phenyl, tolyl, and naphthyl, and aromatic heterocyclic groups, such as furyl, thienyl, pyrrolyl, oxazolyl, isoxazolyl, thiazolyl, isothiazolyl, imidazolyl, pyrazolyl, pyridyl, pyrimidinyl, pyridazinyl, pyradinyl, quinolyl, and isoquinolyl.

Examples of aralkyl include benzyl and phenethyl.

Examples of acyl include $C_{1-6}$ aliphatic acyl such as formyl, acetyl, propionyl (propanoyl), butyryl (butanoyl), valeryl (pentanoyl), and hexanoyl, and aromatic acyl (aroyl), such as benzoyl and toluoyl.

Examples of arylsulfonyl include aromatic hydrocarbonsulfonyl, such as phenylsulfonyl (benzenesulfonyl), p-toluenesulfonyl (tosyl), and naphthalenesulfonyl; and aromatic heterocycle-sulfonyl, such as furansulfonyl, thiophenesulfonyl, pyrrolesulfonyl, oxazolesulfonyl, isooxazolesulfonyl, thiazolesulfonyl, isothiazolesulfonyl, imidazolesulfonyl, pyrazolesulfonyl, pyridinesulfonyl, pyrimidinesulfonyl, pyridazinesulfonyl, pyrazinesulfonyl, quinolinesulfonyl, and isoquinolinesulfonyl.

Examples of $C_{1-6}$ alkylsulfonyl include methanesulfonyl (mesyl) and ethanesulfonyl.

Examples of halogen atoms include fluorine, chlorine, bromine, and iodine atoms.

In formulae (I) and (I'), $C_{1-6}$ alkyl and $C_{1-21}$ alkyl represented by $R^1$, $R^2$, or $R^4$ and $C_{2-6}$ alkenyl, $C_{2-6}$ alkynyl, and $C_{1-6}$ alkylsulfonyl represented by $R^1$ may each be substituted with one or more substituents selected from among, for example, an aromatic group, acyl, hydroxyl, carboxyl, a halogen atom, and $C_{1-6}$ alkoxy (e.g., a methoxy, ethoxy, or propoxy group).

In formulae (I) and (I'), an aromatic group, aralkyl, acyl, and arylsulfonyl represented by $R^1$ may each be substituted with one or more substituents selected from among, for example, $C_{1-6}$ alkyl, $C_{2-6}$ alkenyl, $C_{2-6}$ alkynyl, an aromatic group, acyl, hydroxyl, carboxyl, a halogen atom, and $C_{1-6}$ alkoxy (e.g., a methoxy, ethoxy, or propoxy group).

Examples of pharmaceutically acceptable salts of the compound represented by formula (I) include: inorganic acid salts, such as hydrochloride, sulfate, phosphate, hydrobromide, hydroiodide, nitrate, pyrosulfate, and metaphosphate; and organic acid salts, such as citrate, benzoate, acetate, propionate; fumarate, maleate, or sulfonate (e.g., methanesulfonate, p-toluenesulfonate, or naphthalenesulfonate). Also, the compound can be used as alkali metal salt, such as sodium salt or potassium salt, when the compound has a phenolic hydroxyl or carboxyl group.

Among the compounds represented by formula (I), a compound wherein $R^1$ represents a hydrogen atom can be produced by, for example, halogenating a compound represented by formula (I) wherein X represents a hydrogen atom (e.g., melatonin) by the method disclosed in M. Somei, Y. Fukui, M. Hasegawa, N. Oshikiri, and T. Hayashi, Heterocycles, 53, 1725-1736, 2000. Also, a compound represented by formula (I) wherein $R^1$ represents a hydrogen atom and X represents a halogen atom can be produced by halogenating a compound represented by formula (I) wherein $R^1$ represents hydroxyl and X represents a hydrogen atom (e.g., 1-hydroxymelatonin).

Among the compounds represented by formula (I), a compound wherein $R^1$ represents substituted or unsubstituted $C_{1-6}$ alkyl, substituted or unsubstituted $C_{2-6}$ alkenyl, substituted or unsubstituted $C_{2-6}$ alkynyl, a substituted or unsubstituted aromatic group, substituted or unsubstituted aralkyl, substituted or unsubstituted acyl, substituted or unsubstituted arylsulfonyl, or substituted or unsubstituted $C_{1-6}$ alkylsulfonyl can be produced by, for example, allowing the compound represented by formula (I) wherein X represents a halogen atom obtained in the above-described manner to react with the compound represented by formula $R^1$-X (wherein $R^1$ is as defined above, and X represents a halogen atom) in an organic solvent, such as N,N-dimethylformamide (hereafter abbreviated to "DMF"), in the presence of a base catalyst.

Among the compounds represented by formula (I), a compound wherein $R^1$ represents hydroxyl can be produced by, for example, treating the compound represented by formula (I) wherein X represents a halogen atom obtained in the above-described manner with hydrogen peroxide and sodium tungstate.

Among the compounds represented by formula (I), a compound wherein $R^4$ represents a hydrogen atom can be produced by, for example, halogenating a compound represented by formula (I) wherein X and $R^4$ each represent a hydrogen atom (e.g., $R^1$, $R^3$, $R^5$, and $R^6$ each represent a hydrogen atom) (e.g., treating it with the use of an acetic acid or chloroform solvent, and a brominating agent such as bromine or N-bromosuccinimide).

The compound represented by formula (I) may be hydrolyzed in the presence of a base catalyst to eliminate acyl (—CO—$R^2$), followed by treatment with an acid anhydride ($R^{2'}$CO—O—$COR^{2'}$) or the like and introduction of another acyl. Thus, acyl can be converted. In such a case, since an intermediate deacylation product is generally likely to be oxidized in the air, the deacylation product is preferably used in the next acylation process without purification.

Among the compounds represented by formula (I'), a compound wherein X represents a hydrogen atom and at least one of $R^3$, $R^5$, and $R^6$ represents a chlorine atom is a novel compound. Such a compound is useful as a therapeutic agent for osteoporosis or as an intermediate for synthesizing a compound represented by formula (I') wherein X represents a halogen atom and at least one of $R^3$, $R^5$, and $R^6$ represents a chlorine atom.

Among the compounds represented by formula (I'), a compound wherein X represents a hydrogen atom and at least one of $R^3$, $R^5$ and $R^6$ represents a chlorine atom can be produced by, for example, protecting position 1 of an N-acyl-2,3-dihydrotryptamine derivative (e.g., 2,3-dihydromelatonin) wherein at least one of positions 4, 6, and 7 is a hydrogen atom as described in Examples 10 to 13 with tert-butoxycarbonyl or the like, chlorinating the same with N-chlorosuccinimide or the like, deprotecting the same, and treating the same with active manganese dioxide or the like, followed by dehydrogenation.

The thus-obtained product may be purified by conventional techniques, such as column chromatography using a carrier such as silica gel, or recrystallization using methanol, ethanol, chloroform, dimethylsulfoxide, or water.

Examples of elution solvents for column chromatography include methanol, ethanol, chloroform, acetone, hexane, dichloromethane, ethyl acetate, and a mixed solvent comprised of any thereof.

The compound represented by formula (I) and a pharmaceutically acceptable salt thereof (hereafter referred to as "2-haloindole derivative (I)") has functions of activating osteoblasts and suppressing osteoclasts. Such compound is useful for a pharmaceutical composition for various bone-related diseases, such as a pharmaceutical composition for preventing or treating osteoporosis, or as an osteoblast activator and an osteoclast suppressor, in various fields, such as regenerative medicine, dentistry, or production of edible meats or eggs via fish cultivation or healthy development of livestock. The compound has radical scavenger activity and thus is useful as a pharmaceutical composition for preventing or treating insomnia or lifestyle-related diseases.

The therapeutic agent for osteoporosis of the present invention can be used in combination with, for example, another therapeutic agent for osteoporosis, such as a calcium, vitamin D, hormone, calcitonin, bisphosphonate, or ipriflavone preparation. In such a case, the dose described below can be adequately decreased or increased, according to need.

Hereafter, the dose and the preparation of 2-haloindole derivative (I) are described.

2-Haloindole derivative (I) can be administered to animals or humans alone or in combination with a conventional pharmaceutical carrier. Dosage form is not particularly limited, and it is adequately selected according to need. For example, dosage forms can be oral preparations, such as tablets, capsules, granules, fine granules, powders, controlled-release agents, suspensions, emulsions, syrups, or elixirs or parenteral preparations, such as injections, suppositories, endermic liniments, or adhesive preparations.

Oral preparations are produced in accordance with conventional techniques using excipients, such as starch, lactose, sucrose, mannite, carboxymethylcellulose, cornstarch, or inorganic salt.

In addition to such excipients, this type of preparation can adequately comprise, for example, a binder, a disintegrator, a surfactant, a lubricant, a flow promoter, a flavoring agent, a colorant, or a fragrant material.

Examples of binders include starch, dextrin, powdered acacia, gelatin, hydroxypropyl starch, methylcellulose, carboxymethylcellulose sodium, hydroxypropylcellulose, crystalline cellulose, ethyl cellulose, polyvinylpyrrolidone, and macrogol.

Examples of disintegrators include starch, hydroxypropyl starch, carboxymethylcellulose sodium, carboxymethylcellulose calcium, carboxymethylcellulose, and low-substituted hydroxypropylcellulose.

Examples of surfactants include sodium lauryl sulfate, soybean lecithin, sucrose fatty acid ester, and polysorbate 80.

Examples of lubricants include talc, waxes, hydrogenated vegetable oil, sucrose fatty acid ester, magnesium stearate, calcium stearate, aluminum stearate, and polyethylene glycol.

Examples of flow promoters include light anhydrous silicic acid, dried aluminum hydroxide gel, synthetic aluminum silicate, and magnesium silicate.

Injections are produced in accordance with conventional techniques. In general, diluents, such as distilled water for injection, physiological saline, aqueous glucose solution, olive oil, sesame oil, peanut oil, soybean oil, corn oil, propylene glycol, or polyethylene glycol, can be used. A disinfectant, a preservative, or a stabilizer may further be added, according to need. From the viewpoint of safety, injections may be filled in a vial or the like, frozen, and then dehydrated via a conventional lyophilization technique. An injection solution can be prepared from the lyophilization product immediately before use. According to need, an isotonizing agent, a stabilizer, a preservative, a soothing agent, or the like may further be added.

Examples of other parenteral preparations include endermic liniments, such as a liquid for external use and ointments, adhesive preparations, and suppositories for intrarectal administration. These preparations can be prepared in accordance with conventional techniques.

The preparation of the present invention can be administered once to several times per day to once to several times per week to month, although administration frequency varies depending on dosage form, route of administration, and the like.

In order to achieve desirable effects of oral preparations, 1 to 200 mg of 2-haloindole derivative (I) is generally administered to an adult patient in several separate doses per day, although such amount varies depending on the age, body weight, and severity of symptoms of the patient.

In order to achieve desirable effects of parenteral preparations, 1 to 50 mg of 2-haloindole derivative (I) is generally administered to an adult patient via intravenous injection, intravenous drip infusion, hypodermic injection, or intramuscular injection, although such amount varies depending on the age, body weight, and severity of symptoms of the patient.

This description includes part or all of the contents as disclosed in the description and/or the drawings of Japanese Patent Application No. 2004-64408, which is a priority document of the present application.

EXAMPLES

The present invention is hereafter described in greater detail with reference to examples. These examples, however, are not intended to limit the technical scope of the present invention.

Example 1

Synthesis of 2,4,6-tribromo-1-propargylmelatonin (N-acetyl-2,4,6-tribromo-5-methoxy-1-propargylindole-3-ethanamine) from 2,4,6-tribromomelatonin

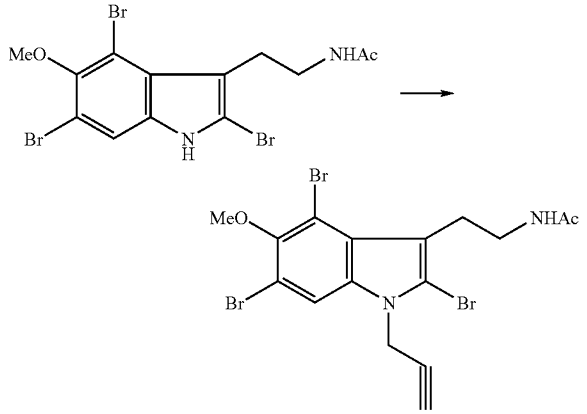

2,4,6-Tribromomelatonin (N-acetyl-2,4,6-tribromo-5-methoxyindole-3-ethanamine) (30.1 mg, 0.064 mmol) (M. Somei, Y. Fukui, M. Hasegawa, N. Oshikiri, and T. Hayashi, Heterocycles, 53, 1725-1736, 2000) was dissolved in 2.0 ml of DMF. To the resulting solution, 31.9 mg (0.22 mmol) of potassium carbonate was added, and the mixture was stirred at room temperature for 5 minutes. Propargyl chloride (0.09 ml, 1.28 mmol) was added to the solution, and the mixture was stirred at room temperature for 4 hours. Water and a mixed solvent of ethyl acetate/methanol (95:5, v/v) were added to the reaction solution, the mixture was stirred, and an organic phase was separated. An aqueous phase was extracted three times with the use of a mixed solvent of ethyl acetate/methanol (95:5, v/v). The organic phase was combined with the extract, washed with saturated saline, and then dried over sodium sulfate. Thereafter, the solvent was removed by distillation under reduced pressure to obtain an yellow oil product. The product was purified via column chromatography using silica gel as a carrier and ethyl acetate as an eluent. Thus, the target compound was obtained with a yield of 31.6 mg (97%). A colorless needle crystal was obtained via recrystallization from ethyl acetate/hexane.

mp: 199° C. to 200° C.

IR (KBr): 3286, 1628, 1558, 1456, 1435, 1410, 1294, 1018 $cm^{-1}$ $^1H$-NMR ($CDCl_3$) δ: 1.93 (3H, s), 2.34 (1H, t, J=2.4 Hz), 3.23 (2H, t, J=6.6 Hz), 3.58 (2H, dt, J=2.9, 6.6 Hz, changed into t, J=6.6 Hz via deuteration), 3.89 (3H, s), 4.91 (2H, d, J=2.4 Hz), 5.54 (1H, br t, J=6.6 Hz, eliminated via deuteration), 7.58 (1H, s)

Anal. Calcd for $C_{16}H_{15}Br_3N_2O_2$: C, 37.90; H, 2.98; N, 5.53. Found: C, 37.78; H, 3.00; N, 5.44

Example 2

Synthesis of 1-allyl-2,4,6-tribromomelatonin (N-acetyl-1-allyl-2,4,6-tribromo-5-methoxyindole-3-ethanamine) from 2,4,6-tribromomelatonin

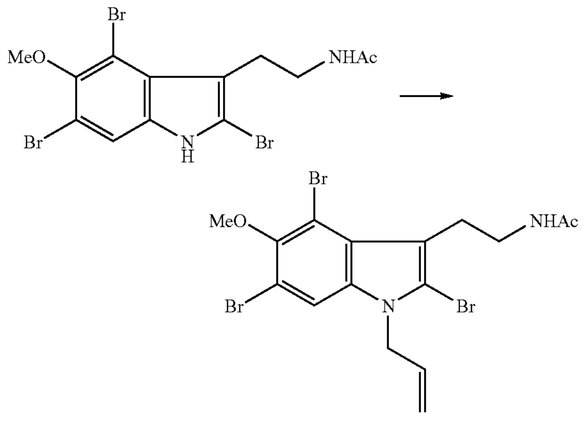

2,4,6-Tribromomelatonin (N-acetyl-2,4,6-tribromo-5-methoxyindole-3-ethanamine) (30.2 mg, 0.064 mmol) was dissolved in 2.0 ml of DMF, 31.1 mg (0.22 mmol) of potassium carbonate was added to the resulting solution, and the mixture was stirred at room temperature for 5 minutes. To this solution, 0.11 ml (1.28 mmol) of allyl bromide was added, and the mixture was stirred at room temperature for 1.5 hours. Water and a mixed solvent of ethyl acetate/methanol (95:5, v/v) were added to the reaction solution, the mixture was stirred, and an organic phase was then separated. An aqueous phase was further extracted three times with a mixed solvent of ethyl acetate/methanol (95:5, v/v). The organic phase was combined with the extract, washed with saturated saline, and then dried over sodium sulfate. Thereafter, the solvent was removed by distillation under reduced pressure to obtain an yellow oil product. The product was purified via column chromatography using silica gel as a carrier and ethyl acetate as an eluent. Thus, the target compound was obtained with a yield of 31.0 mg (95%). A colorless needle crystal was obtained via recrystallization from ethyl acetate/hexane.

mp: 142° C. to 143° C.

IR (KBr): 3284, 1633, 1562, 1456, 1412, 1298, 1018 $cm^{-1}$ $^1$H-NMR ($CDCl_3$) δ: 1.93 (3H, s), 3.24 (2H, t, J=6.6 Hz), 3.58 (2H, q, J=6.6 Hz), 3.89 (3H, s), 4.76 (2H, dt, J=4.9, 1.7 Hz), 4.89 (1H, d, J=16.6 Hz), 5.20 (1H, d, J=10.3 Hz), 5.55 (1H, br t, eliminated via deuteration), 5.87 (1H, ddt, J=16.6, 10.3, 4.9 Hz), 7.4 (1H, s)

Anal. Calcd for $C_{16}H_{17}Br_3N_2O_2$: C, 37.75; H, 3.37; N, 5.50. Found: C, 37.75; H, 3.37; N, 5.42

Example 3

Synthesis of 1-benzyl-2,4,6-tribromomelatonin. (N-acetyl-1-benzyl-2,4,6-tribromo-5-methoxyindole-3-ethanamine) from 2,4,6-tribromomelatonin

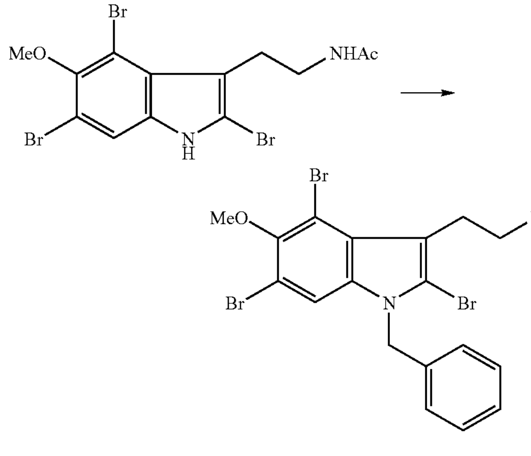

2,4,6-Tribromomelatonin (N-acetyl-2,4,6-tribromo-5-methoxyindole-3-ethanamine) (40.1 mg, 0.086 mmol) was dissolved in 2.0 ml of DMF, 41.4 mg (0.30 mmol) of potassium carbonate was added thereto, and the mixture was stirred at room temperature for 5 minutes. To this solution, 0.20 ml (1.72 mmol) of benzyl bromide was added, and the mixture was stirred at room temperature for 1 hour. Water and a mixed solvent of ethyl acetate/methanol (95:5, v/v) were added to the reaction solution, the mixture was stirred, and an organic phase was separated. An aqueous phase was further extracted three times with a mixed solvent of ethyl acetate/methanol (95:5, v/v). The organic phase was combined with the extract, washed with saturated saline, and then dried over sodium sulfate. Thereafter, the solvent was removed by distillation under reduced pressure to obtain an yellow oil product. The product was purified via column chromatography using silica gel as a carrier and ethyl acetate as an eluent. Thus, the target compound was obtained with a yield of 40.3 mg (83%). A colorless needle crystal was obtained via recrystallization from ethyl acetate/hexane.

mp: 218° C. to 219° C.

IR (KBr): 3280, 1630, 1547, 1454, 1414, 1360, 1298, 1014 $cm^{-1}$ $^1$H-NMR ($CDCl_3$) δ: 1.91 (3H, s), 3.26 (2H, t, J=6.6 Hz), 3.61 (2H, td, J=12.7, 6.6 Hz), 3.88 (3H, s), 5.36 (2H, s), 5.54 (1H, br t, J=6.6 Hz, eliminated via deuteration), 7.01 (2H, d, J=6.6 Hz), 7.27-7.33 (3H, m), 7.39 (1H, s)

Anal. Calcd for $C_{20}H_{19}Br_3N_2O_2$: C, 42.97; H, 3.43; N, 5.01. Found: C, 42.76; H, 3.40; N, 4.86

Example 4

Synthesis of 2,4,6-tribromo-1-tosyl-melatonin (N-acetyl-2,4,6-tribromo-5-methoxy 1-tosylindole-3-ethanamine) from 2,4,6-tribromomelatonin

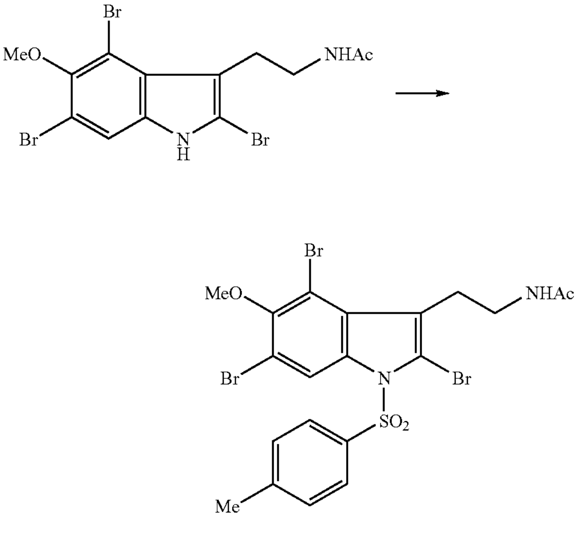

2,4,6-Tribromomelatonin (N-acetyl-2,4,6-tribromo-5-methoxyindole-3-ethanamine) (40.5 mg, 0.086 mmol) was dissolved in 2.0 ml of DMF, 4.1 mg (0.10 mmol) of sodium hydride was added thereto, and the mixture was stirred in a nitrogen atmosphere at room temperature for 10 minutes. To this solution, 348.0 mg (1.30 mmol) of tosyl chloride was added, and the mixture was stirred at room temperature for 1 hour. Saturated saline was added to the reaction solution, and extraction was carried out three times with the use of a mixed solvent of chloroform/methanol (95:5, v/v). The extract was washed with saturated saline and then dried over sodium sulfate. Thereafter, the solvent was removed by distillation under reduced pressure to obtain an oil product. The product was purified via column chromatography using silica gel as a carrier and a mixed solvent of chloroform/methanol (98:2, v/v) as an eluent. Thus, the target compound was obtained with a yield of 40.4 mg (75%). A colorless needle crystal was obtained via recrystallization from chloroform/hexane.

mp: 215° C. to 216° C.

IR (KBr): 3305, 1628, 1541, 1454, 1392, 1200, 1174 $cm^{-1}$ $^1$H-NMR ($CDCl_3$) δ: 1.88 (3H, s), 2.40 (3H, s), 3.18 (2H, t, J=6.6 Hz), 3.49 (2H, q, J=6.6 Hz), 3.90 (3H, s), 5.42 (1H, br t, eliminated via deuteration), 7.27 (2H, d, J=7.5 Hz), 7.74 (2H, d, J=7.5 Hz), 8.59 (1H, s)

Anal. Calcd for $C_{20}H_{19}Br_3N_2O_4S$: C, 38.55; H, 3.07; N, 4.50. Found: C, 38.28; H, 3.15; N, 4.30

Example 5

Synthesis of 2,7-dibromomelatonin (1a), 2,4-dibromomelatonin (1b), 7-bromomelatonin (2a), and 4,7-dibromomelatonin (2b) from 1-hydroxymelatonin

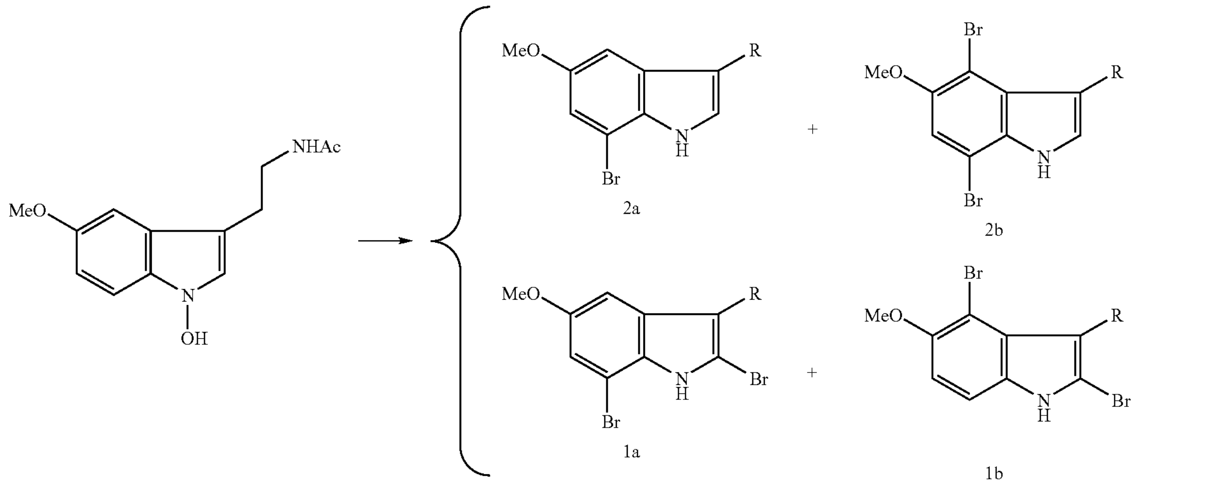

2a

2b

1a

1b

R = $CH_2CH_2NHAc$

1-Hydroxymelatonin (101.0 mg, 0.41 mmol) (M. Somei, N. Oshikiri, M. Hasegawa, and F. Yamada, Heterocycles, 51, 1237-1242, 1999) was dissolved in 5.0 ml of acetic acid, 0.68 ml (0.39 mmol) of a solution of 0.57 M bromine in acetic acid was added thereto, and the mixture was stirred at room temperature for 5 hours. An aqueous solution of 10% sodium thiosulfate was added to the reaction solution, and an aqueous solution of 20% sodium hydroxide was added thereto under ice cooling to neutralize the reaction solution. The entire product was subjected to extraction three times with a mixed solvent of chloroform/methanol (95:5, v/v). The extract was washed with saturated saline and then dried over sodium sulfate. Thereafter, the solvent was removed by distillation under reduced pressure to obtain an oil product. The product was purified via column chromatography using silica gel as a carrier and a mixed solvent of chloroform/methanol (98:2, v/v) as an eluent. In the order of elution, 12.0 mg of 2,7-dibromomelatonin (1a) (8%), 20.0 mg of 2,4-dibromomelatonin (1b) (13%), 7.1 mg of 7-bromomelatonin (2a) (6%), 18.4 mg of 4,7-dibromomelatonin (2b) (12%), and 8.8 mg (9%) of unreacted raw material were obtained.

7-Bromomelatonin (2a)

Properties: colorless oil product.

IR (KBr): 3209, 1653, 1541, 1489, 1043, 829 $cm^{-1}$ $^1$H-NMR ($CDCl_3$) δ: 1.93 (3H, s), 2.92 (2H, t, J=6.7 Hz), 3.57 (2H, q, J=6.7 Hz, changed into t, J=6.7 Hz via deuteration), 3.85 (3H, s), 5.51 (1H, br s, eliminated via deuteration), 7.00 (1H, d, J=1.7 Hz), 7.06 (1H, d, J=1.7 Hz), 7.07 (1H, d, J=2.0 Hz, changed into s via deuteration), 8.09 (1H, br s, eliminated via deuteration).

High-resolution mass spectrometry (m/z): Calcd for $C_{13}H_{15}BrN_2O_2$: 310.0316, 312.0297.

Found: 310.0320, 312.0304.

4,7-Dibromomelatonin (2b)

mp: 212° C. to 213° C. (decomposition point: a colorless powdery crystal is obtained via recrystallization from chloroform/hexane).

IR (KBr): 3269, 1635, 1618, 1558, 1301, 607 $cm^{-1}$.

$^1$H-NMR (DMSO-$d_6$) δ: 1.79 (3H, s), 2.89 (2H, t, J=6.6 Hz), 3.51 (2H, q, J=6.6 Hz, changed into t, J=6.6 Hz via deuteration), 3.84 (3H, s), 5.45 (1H, br s, eliminated via deuteration), 7.02 (1H, d, J=2.2 Hz, changed into s via deuteration), 6.95 (1H, d, J=2.1 Hz), 7.03 (1H, d, J=2.1 Hz), 8.05 (1H, br s, eliminated via deuteration).

Mass spectrometry (m/z): 388 ($M^+$), 390 ($M^+$), 392 ($M^+$).

Anal. Calcd for $C_{13}H_{14}Br_2N_2O_2$.⅛$H_2O$: C, 39.80; H, 3.66; N, 7.14. Found: C, 39.62; H, 3.63; N, 7.06.

2,7-Dibromomelatonin (1a)

mp: 211° C. to 213° C. (decomposition point: colorless powdery crystal is obtained via recrystallization from chloroform/hexane)

IR (KBr): 3114, 1643, 1626, 1568, 1487, 1078, 825 $cm^{-1}$ $^1$H-NMR ($CDCl_3$) δ: 1.93 (3H, s), 2.89 (2H, t, J=6.6 Hz), 3.51 (2H, q, J=6.6 Hz, changed into t, J=6.6 Hz via deuteration), 3.84 (3H, s), 5.45 (1H, br s, eliminated via deuteration), 7.02 (1H, d, J=2.2 Hz, changed into s via deuteration), 6.95 (1H, d, J=2.1 Hz), 7.03 (1H, d, J=2.1 Hz), 8.05 (1H, br s, eliminated via deuteration)

Mass spectrometry (m/z): 388, 390, 392 ($M^+$)

Anal. Calcd for $C_{13}H_{14}Br_2N_2O_2$.¼$H_2O$: C, 39.57; H, 3.70; N, 7.10. Found: C, 39.57; H, 3.61; N, 6.94

2,4-Dibromomelatonin (1b)

Properties of the target compound were consistent with those of compound II described in M. Somei, Y. Fukui, M. Hasegawa, N. Oshikiri, and T. Hayashi, Heterocycles, 53, 1725-1736, 2000.

Example 6

Synthesis of 2,4,7-tribromomelatonin (1d), 2,4,6,7-tetrabromomelatonin (1e), 2,4,6-tribromomelatonin (1c), and 3-(2-acetamidoethyl)-3,4,7-tribromo-5-methoxy-2-oxoindoline (2c) from 1-hydroxymelatonin

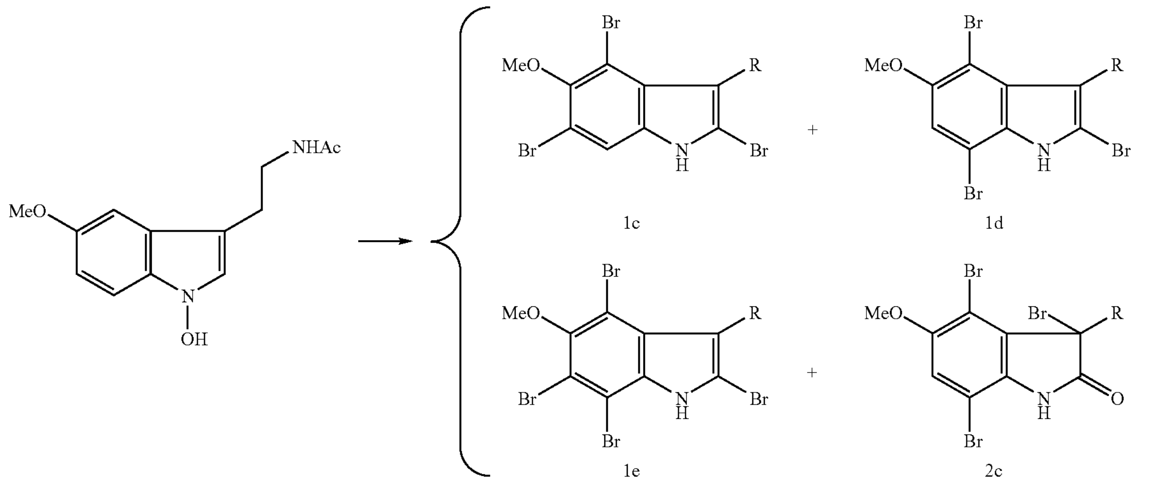

1c 1d 1e 2c

R = $CH_2CH_2NHAc$

1-Hydroxymelatonin (54.1 mg, 0.22 mmol) was dissolved in 3.0 ml of acetic acid, 1.14 ml (0.65 mmol) of a solution of 0.57 M bromine in acetic acid was added thereto, and the mixture was stirred at room temperature for 2 hours. The product was purified via the same post-treatment and column chromatography as that carried out in Example 5, and 22.6 mg of 2,4,7-tribromomelatonin (1d) (22%), 21.0 mg of 2,4,6,7-tetrabromomelatonin (1e) (18%), 2.7 mg of 2,4,6-tribromomelatonin (1c) (3%), and 10.3 mg of 3-(2-acetamidoethyl)-3,4,7-tribromo-5-methoxy-2-oxoindoline (2c) (9%) were obtained in the order of elution.

2,4,7-Tribromomelatonin (1d)

mp: 220° C. to 221° C. (decomposition point: a colorless powdery crystal is obtained via recrystallization from chloroform/hexane)

IR (KBr): 3140, 1674, 1550, 1527, 1300, 1107, 1066 $cm^{-1}$ $^1H$-NMR ($CDCl_3$) δ: 1.93 (3H, s), 3.19 (2H, t, J=6.6 Hz), 3.59 (2H, q, J=6.6 Hz, changed into t, J=6.6 Hz via deuteration), 3.91 (3H, s), 5.55 (1H, br s, eliminated via deuteration), 7.05 (1H, s), 8.25 (1H, br s, eliminated via deuteration)

Anal. Calcd for $C_{13}H_{13}Br_3N_2O_2$: C, 33.29; H, 2.79; N, 5.97. Found: C, 33.27; H, 2.87; N, 5.94

2,4,6,7-Tetrabromomelatonin (1e)

mp: 232° C. to 234° C. (decomposition point: a colorless columnar crystal is obtained via recrystallization from chloroform/hexane)

IR (KBr): 3095, 1624, 1576, 1433, 1288, 1039 $cm^{-1}$ $^1H$-NMR (DMSO-$d_6$) δ: 1.77 (3H, s), 2.99 (2H, t, J=7.0 Hz), 3.27 (2H, q, J=7.0 Hz), 3.79 (3H, s), 7.88 (1H, br t, J=7.0 Hz), 12.33 (1H, br s, eliminated via deuteration)

Anal. Calcd for $C_{13}H_{12}Br_4N_2O_2$: C, 28.50; H, 2.21; N, 5.11. Found: C, 28.25; H, 2.29; N, 4.84

3-(2-Acetamidoethyl)-3,4,7-tribromo-5-methoxy-2-oxoindoline (2c)

Properties: an yellow oil product

IR (film): 3261, 1734, 1653, 1466, 1435, 1298, 754 $cm^{-1}$ $^1H$-NMR ($CDCl_3$) δ: 1.83 (3H, s), 2.70-2.76 (1H, m), 3.10-3.19 (3H, m), 3.88 (3H, s), 5.53 (1H, br s, eliminated via deuteration), 6.95 (1H, s), 8.04 (1H, br s, eliminated via deuteration)

High-resolution mass spectrometry (m/z): Calcd for $C_{13}H_{14}Br_3N_2O_3$: 482.8554, 484.8534, 486.8513, 488.8493. Found: 482.8508, 484.8505, 486.8502, 488.8497

2,4,6-Tribromomelatonin (1c)

The properties of the target compound were consistent with those of compound 12 described in M. Somei, Y. Fukui, M. Hasegawa, N. Oshikiri, and T. Hayashi, Heterocycles, 53, 1725-1736, 2000.

Example 7

Synthesis of 4,7-dibromomelatonin (2b), 2,4,7-tribromomelatonin (1d), and 3-(2-acetamidoethyl)-4,7-dibromo-5-methoxy-2-oxoindoline (2d) from 1-methoxymelatonin

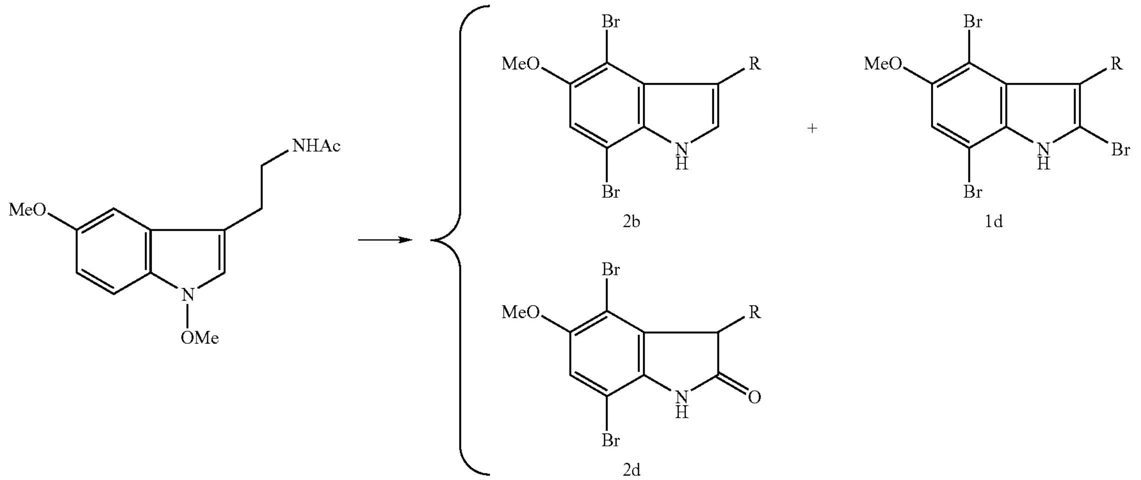

2b 1d 2d

R = $CH_2CH_2NHAc$

1-Methoxymelatonin (107.9 mg, 0.41 mmol) was dissolved in 5.0 ml of acetic acid, 0.70 ml (0.40 mmol) of a solution of 0.57 M bromine in acetic acid was added thereto, and the mixture was stirred at room temperature for 2 hours. The product was purified via the same post-treatment and column chromatography as that carried out in Example 5, and 71.4 mg of 2,4,7-tribromomelatonin (1d) (37%), 18.4 mg of 4,7-dibromomelatonin (2b) (11%), and 26.1 mg of 3-(2-acetamidoethyl)-4,7-dibromo-5-methoxy-2-oxoindoline (2d) (16%) were obtained in the order of elution.

[3-(2-Acetamidoethyl)-4,7-dibromo-5-methoxy-2-oxoindoline (2d)]

mp: 224° C. to 225° C. (decomposition point: a colorless powdery crystal of chloro form/m ethanol/hexane)

IR (KBr): 3296, 1712, 1625, 1545, 1460, 1431, 1306, 1286 $cm^{-1}$ $^1$H-NMR ($CDCl_3$) δ: 1.93 (3H, s), 2.26 (1H, dqd, J=13.4, 8.1, 2.4 Hz), 2.54 (1H, dtd, J=13.4, 6.6, 3.2 Hz), 3.37 (2H, qd, J=6.6, 2.4 Hz, changed into td, J=6.6 Hz, 2.4 Hz via deuteration), 3.65 (1H, dd, J=8.1, 3.2 Hz), 3.86 (3H, s), 5.99 (1H, br s, eliminated via deuteration), 6.88 (1H, s), 7.52 (1H, br s, eliminated via deuteration)

Mass spectrometry (m/z): 404, 406, 408 ($M^+$)

Anal. Calcd for $C_{13}H_{14}Br_2N_2O_3.½H_2O$: C, 37.62; H, 3.64; N, 6.75. Found: C, 37.84; H, 3.47; N, 6.75

Example 8

Synthesis of 2,4,6-tribromo-5-methoxytryptamine (2e) from 2,4,6-tribromomelatonin (1c)

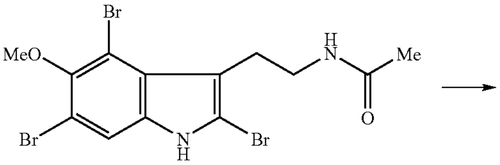

1c

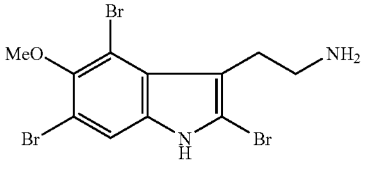

2e 2,4,6-Tribromomelatonin (1c) (103.6 mg, 0.22 mmol) was dissolved in 2.0 ml of methanol, an aqueous solution of 40% sodium hydroxide (2.0 ml, 33.4 mmol) was added thereto, and the mixture was stirred under reflux for 5 hours. Water was added to the reaction solution, and extraction was carried out with the use of a mixed solvent of chloroform/methanol (9:1, v/v). The extract was washed with saturated saline and then dried over sodium sulfate, followed by removal of the solvent by distillation. The residue was purified via column chromatography using silica gel as a carrier and a mixed solvent of chloroform/methanol/28% aqueous ammonia (46:3:0.3, v/v) as an eluent. Thus, the target compound, which was an unstable colorless crystal colored upon oxidization in the air, was obtained with a yield of 71.3 mg (76%).

mp: 70° C. (decomposition)

IR (KBr): 2931, 2868, 1583, 1552, 1452, 1403, 1300 $cm^{-1}$ $^1$H-NMR (DMSO-$d_6$) δ: 2.77 (2H, t, J=7.6 Hz), 2.95 (2H, t, J=7.6 Hz), 3.31 (3H, br s), 3.77 (3H, s), 7.50 (1H, s)

High-resolution mass spectrometry (FAB+) (m/z): Calcd for $C_{11}H_{12}Br_3N_2O$: 424.8500, 426.8479, 428.8459, 430.8439. Found: 424.8524, 426.8507, 428.8474, 430.8463

Example 9

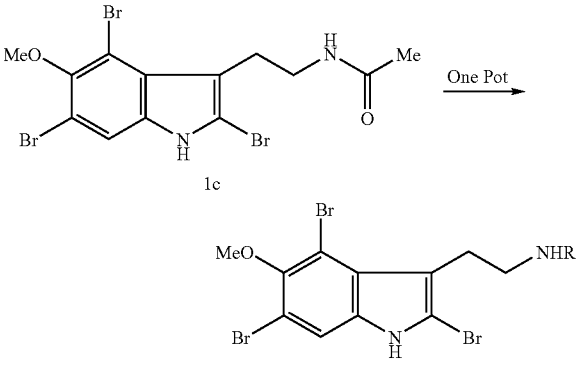

1c

3 a) R = valeryl
b) R = nonanoyl
c) R = palmitoyl
d) R = cyclopropylcarbonyl

(1) Synthesis of 2,4,6-tribromo-5-methoxy-N-valeryltryptamine (3a) from 2,4,6-tribromomelatonin (1c)

2,4,6-Tribromomelatonin (1c) (104.5 mg, 0.22 mmol) was dissolved in 2.0 ml of methanol, an aqueous solution of 40% sodium hydroxide (2.0 ml, 33.4 mmol) was added thereto, and the mixture was stirred under reflux for 5 hours. Water was added to the reaction solution, and extraction was carried out with the use of a mixed solvent of chloroform/methanol (9:1, v/v). The extract was washed with saturated saline and then dried over sodium sulfate, followed by removal of the solvent by distillation. The obtained 2,4,6-tribromo-5-methoxytryptamine (2e) was dissolved in 3.0 ml of anhydrous chloroform without purification. To this solution, a solution of acid anhydride prepared from 23.0 mg (0.23 mmol) of triethylamine, 21.2 mg (0.22 mmol) of methyl chlorocarbonate, and 23.0 mg (0.22 mmol) of valeric acid in 3.0 ml of chloroform was added, and the mixture was stirred at room temperature for 1 hour. Water was added to the reaction solution, and extraction was carried out with the use of a mixed solvent of chloroform/methanol (95:5, v/v). The extract was washed with saturated saline and then dried over sodium sulfate, followed by removal of the solvent by distillation. The residue was purified via column chromatography using silica gel as a carrier and chloroform as an eluent. The target compound was obtained with a yield of 77.9 mg (68%). A colorless plate crystal was obtained via recrystallization from chloroform/hexane.

mp: 74° C. to 79° C.

IR (KBr): 2960, 1624, 1520, 1404, 1300 $cm^{-1}$ $^1$H-NMR ($CDCl_3$) δ: 0.88 (3H, t, J=7.3 Hz), 1.29 (2H, sex, J=7.3 Hz), 1.56 (2H, quint, J=7.3 Hz), 2.13 (2H, t, J=7.3 Hz), 3.18 (2H, t, J=6.6 Hz), 3.61 (2H, q, J=6.6 Hz, changed into t, J=6.6 Hz via deuteration), 3.88 (3H, s), 5.63 (1H, br t, J=6.6 Hz, eliminated via deuteration), 7.44 (1H, s), 8.69 (1H, br s, eliminated via deuteration)

High-resolution mass spectrometry (m/z): Calcd for $C_{16}H_{19}Br_3N_2O_2$: 507.8996, 509.8976, 511.8956, 513.8935. Found: 507.8969, 509.8982, 511.8975, 513.8917

(2) Synthesis of 2,4,6-tribromo-5-methoxy-N-nonanoyltryptamine (3b) from 2,4,6-tribromomelatonin (1c)

Instead of valeric acid used in the method for synthesizing 2,4,6-tribromo-5-methoxy-N-valeryltryptamine (3a) of (1), nonanoic acid was used to carry out the same reaction and post-treatment, and the target compound (3b) was synthesized with a yield of 72%. A colorless powdery crystal was obtained via recrystallization from chloroform/hexane.

mp: 58° C. to 62° C.

IR (KBr): 2922, 1606, 1550, 1414, 1302 $cm^{-1}$ $^1$H-NMR ($CDCl_3$) δ: 0.87 (3H, t, J=6.9 Hz), 1.21-1.31 (10H, m), 1.52-1.60 (2H, m), 2.12 (2H, t, J=7.7 Hz), 3.18 (2H, t, J=6.6 Hz), 3.60 (2H, q, J=6.6 Hz, change into t, J=6.6 Hz via deuteration), 3.88 (3H, s), 5.58 (1H, br t, J=6.6 Hz, eliminated via deuteration), 7.45 (1H, s), 8.41 (1H, s, eliminated via deuteration)

Mass spectrometry (m/z): 564, 566, 568, 570 ($M^+$)

Anal. Calcd for $C_{20}H_{27}Br_3N_2O_2.H_2O$: C, 41.05; H, 5.00; N, 4.79. Found: C, 40.93; H, 5.05; N, 4.95

(3) Synthesis of 2,4,6-tribromo-5-methoxy-N-palmitoyltryptamine (3c) from 2,4,6-tribromomelatonin (1c)

Instead of valeric acid used in the method for synthesizing 2,4,6-tribromo-5-methoxy-N-valeryltryptamine (3a) of (1), palmitic acid was used to carry out the same reaction and post-treatment, and the target compound (3c) was synthesized with a yield of 72%. A colorless powdery crystal was obtained via recrystallization from chloroform/hexane.

mp: 107° C. to 108° C.

IR (KBr): 2918, 2850, 1618, 1550, 1410, 1298 $cm^{-1}$ $^1$H-NMR ($CDCl_3$) δ: 0.88 (3H, t, J=6.9 Hz), 1.22-1.27 (24H, m), 1.53-1.59 (2H, m), 2.12 (2H, t, J=7.7 Hz), 3.18 (2H, t, J=6.6 Hz), 3.61 (2H, q, J=6.6 Hz, changed into t, J=6.6 Hz via deuteration), 3.88 (3H, s), 5.61 (1H, br t, J=6.6 Hz, eliminated via deuteration), 7.44 (11H, s), 8.62 (11H, br s, eliminated via deuteration)

Mass spectrometry (m/z): 662, 664, 666, 668 ($M^+$)

Anal. Calcd for $C_{27}H_{41}Br_3N_2O_2.½H_2O$: C, 48.09; H, 6.28; N, 4.15. Found: C, 48.15; H, 6.34; N, 4.17

(4) Synthesis of 2,4,6-tribromo-5-methoxy-N-cyclopropylcarbonyltryptamine (3d) from 2,4,6-tribromomelatonin (1c)

Instead of valeric acid used in the method for synthesizing 2,4,6-tribromo-5-methoxy-N-valeryltryptamine (3a) of (1), cyclopropanecarboxylic acid was used to carry out the same reaction and post-treatment, and the target compound (3d) was synthesized with a yield of 67%. A colorless prism crystal was obtained via recrystallization from chloroform/hexane.

mp: 84° C. to 84.5° C.

IR (KBr): 3421, 1628, 1527, 1404, 1300 $cm^{-1}$

$^1$H-NMR ($CDCl_3$) δ: 0.70 (2H, td, J=7.4, 4.4 Hz), 0.93 (2H, dt, J=7.4, 4.4 Hz), 1.29 (1H, tt, J=7.4, 4.4 Hz), 3.19 (2H, t, J=6.5 Hz), 3.61 (2H, q, J=6.5 Hz, changed into t, J=6.5 Hz via deuteration), 3.88 (3H, s), 5.81 (1H, br t, J=6.5 Hz, eliminated via deuteration), 7.43 (1H, s), 8.60 (1H, br s, eliminated via deuteration)

High-resolution mass spectrometry (m/z): Calcd for $C_{15}H_{15}Br_3N_2O_2$: 491.8683, 493.8663, 495.8643, 497.8622. Found: 491.8698, 493.8634, 495.8635, 497.8594

Anal. Calcd for $C_{15}H_{15}Br_3N_2O_2.H_2O$: C, 35.12; H, 3.34; N, 5.46. Found: C, 34.77; H, 3.00; N, 5.34

Example 10

Synthesis of N-acetyl-1-tert-butoxycarbonyl-2,3-dihydro-5-methoxytryptamine (5) from 2,3-dihydromelatonin (4)

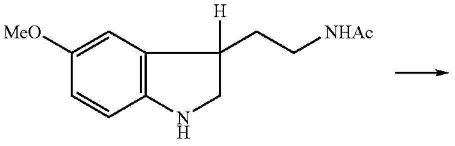

4

-continued

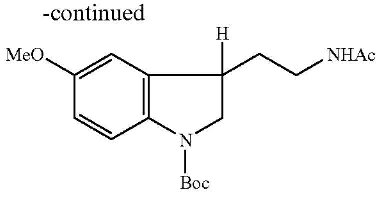

5

2,3-Dihydromelatonin (172.5 mg, 0.737 mmol) (synthesized in accordance with the method reported by M. Somei, Y. Fukui, M. Hasegawa, N. Oshikiri, T. Hayashi, Heterocycles, 53(8), 1725-1736, 2000) and 17.9 mg (0.15 mmol) of 4-dimethylaminopyridine were dissolved in 7.0 ml of chloroform. A solution of 207.8 mg (0.952 mmol) of di-tert-butyl dicarbonate in 2.0 ml of chloroform was added thereto, and the mixture was stirred at room temperature for 10 hours. The solvent was removed by distillation, and the residue was purified via column chromatography using silica gel as a carrier and a mixed solvent of chloroform/methanol (97:3, v/v) as an eluent. The target compound was obtained with a yield of 234.2 mg (95%).

Properties: colorless oil product

IR (KBr): 3278, 1701, 1635 $cm^{-1}$

$^1$H-NMR (DMSO-$d_6$, 90° C.) δ: 1.50 (9H, s), 1.56-1.66 (1H, m), 1.80 (3H, s), 1.82-1.91 (1H, m), 3.13 (2H, q, J=6.4 Hz), 3.22-3.32 (1H, m), 3.56 (1H, dd, J=10.7, 6.4 Hz), 3.71 (3H, s), 4.03 (1H, t, J=10.7 Hz), 6.70 (1H, dd, J=8.5, 2.4 Hz), 6.80 (1H, d, J=2.4 Hz), 7.47 (1H, br d, J=8.5 Hz), 7.55 (1H, br s)

High-resolution mass spectrometry (FAB+) (m/z): Calcd for $C_{18}H_{27}N_2O_4$ ($MH^+$): 335.1971. Found: 335.1966

Example 11

Synthesis of N-acetyl-2,3-dihydro-4,6,7-trichloro-5-methoxytryptamine (8) and N-acetyl-4,6-dichloro-2,3-dihydro-5-methoxytryptamine (9) from N-acetyl-1-tert-butoxycarbonyl-2,3-dihydro-5-methoxytryptamine (5)

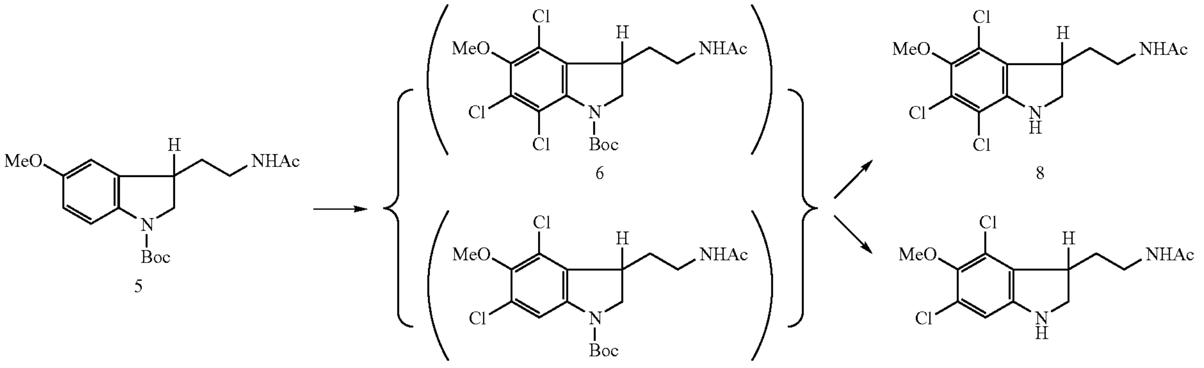

5 6 7 8 9

N-Acetyl-1-tert-butoxycarbonyl-2,3-dihydro-5-methoxytryptamine (5) (76.5 mg, 0.23 mmol) was dissolved in 4.0 ml of chloroform, 92.0 mg (0.69 mmol) of N-chlorosuccinimide was added thereto, and the mixture was refluxed for 3 hours. Chloroform was added to the reaction solution, and the organic phase was washed with saturated saline and then dried over sodium sulfate, followed by removal of the solvent by distillation. The residue was purified via column chromatography using silica gel as a carrier and ethyl acetate as an eluent. As a result, 44.8 mg of a mixture comprising N-acetyl-1-tert-butoxycarbonyl-2,3-dihydro-4,6,7-trichloro-5-methoxytryptamine (6) and N-acetyl-1-tert-butoxycarbonyl-4,6-dichloro-2,3-dihydro-5-methoxytryptamine (7) having the same Rf value was obtained. This mixture was dissolved in 2.0 ml of a mixed solvent of chloroform/trifluoroacetic acid (4:1, v/v), and the mixture was stirred at room temperature for 3 hours. The solvent was removed by distillation, and an aqueous solution of 8% sodium hydroxide was added to the residue for alkalization, followed by extraction with chloroform. The organic phase was washed with saturated saline, and then dried over sodium sulfate, followed by removal of the solvent by distillation. The residue was subjected to separation and purification via column chromatography using silica gel as a carrier and a mixed solvent of chloroform/methanol (97:3, v/v) as an eluent. Thus, 10.1 mg (13%) of compound 8 and 7.3 mg (11%) of compound 9 were obtained in the order of elution.

Compound 8: $^1$H-NMR ($CDCl_3$) δ: 1.83-2.01 (2H, m), 1.97 (3H, s), 3.24-3.41 (2H, m), 3.46-3.56 (2H, m), 3.74 (1H, t, J=9.4 Hz), 3.82 (3H, s), 4.03 (1H, br s), 5.60 (1H, br s)

Compound 9: $^1$H-NMR ($CDCl_3$) δ: 1.58 (1H, br s), 1.82-1.95 (2H, m), 1.96 (3H, s), 3.25-3.35 (2H, m), 3.38-3.47 (2H, m), 3.69 (1H, t, J=8.9 Hz), 3.81 (3H, s), 5.64 (1H, br s), 6.53 (1H, s)

Example 12

Synthesis of 4,6,7-trichloromelatonin (10) from N-acetyl-2,3-dihydro-4,6,7-trichloro-5-methoxytryptamine (8)

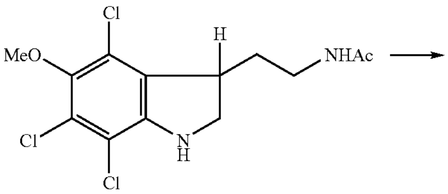

8

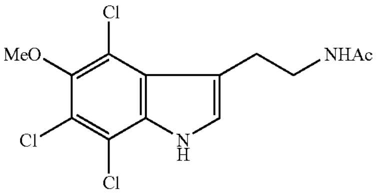

10

N-Acetyl-2,3-dihydro-4,6,7-trichloro-5-methoxytryptamine (8) (10.1 mg, 0.03 mmol) was dissolved in 2.0 ml of chloroform, 41.0 mg (0.47 mmol) of active manganese dioxide was added thereto, and the mixture was stirred at room temperature for 24 hours. After the solvent was removed by distillation, the residue was purified via column chromatography using silica gel as a carrier and a mixed solvent of chloroform/methanol (97:3,v/v) as an eluent. Thus, 9.5 mg (95%) of the target compound was obtained. A colorless needle crystal was obtained via recrystallization from ethyl acetate.

mp: 199° C. to 201° C.

IR (KBr): 3273, 1624 $cm^{-1}$ $^1$H-NMR ($CDCl_3$) δ: 1.96 (3H, s), 3.18 (2H, t, J=6.8 Hz), 3.60 (2H, q, J=6.8 Hz, changed into t, J=6.8 Hz via deuteration), 5.57 (1H, br s, eliminated via deuteration), 7.13 (1H, br d, J=2.4 Hz, changed into s via deuteration), 8.35 (1H, br s, eliminated via deuteration)

High-resolution mass spectrometry ($FAB^+$) (m/z): Calcd for $C_{13}H_{14}Cl_3N_2O_2$ ($MH^+$): 335.0121, 337.0091, 339.0062, 341.0032. Found: 335.0112, 337.0098, 335.0092, 341.0058

Example 13

Synthesis of 4,6-dichloromelatonin (11) from N-acetyl-4,6-dichloro-2,3-dihydro-5-methoxytryptamine (9)

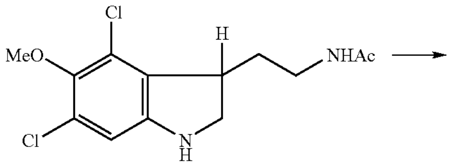

9

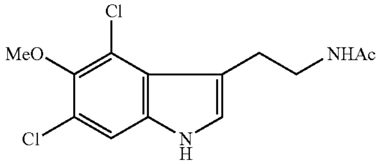

11

N-Acetyl-4,6-dichloro-2,3-dihydro-5-methoxytryptamine (9) (7.3 mg, 0.024 mmol) was dissolved in 2.0 ml of chloroform, 15.0 mg (0.17 mmol) of active manganese dioxide was added thereto, and the mixture was stirred at room temperature for 24 hours. After the solvent was removed by distillation, the residue was purified via column chromatography using silica gel as a carrier and a mixed solvent of chloroform/methanol (97:3, v/v) as an eluent. Thus, 6.2 mg (85%) of the target compound was obtained.

Properties: colorless oil product.

IR (film): 3278, 1653 $cm^{-1}$.

$^1$H-NMR ($CDCl_3$) δ: 1.96 (3H, s), 3.18 (2H, t, J=6.7 Hz), 3.60 (2H, q, J=6.7 Hz, changed into t, J=6.7 Hz via deuteration), 5.58 (1H, br s, eliminated via deuteration), 7.05 (1H, br d, J=2.0 Hz, changed into s via deuteration), 7.28 (1H, s), 8.17 (1H, br s, eliminated via deuteration).

High-resolution mass spectrometry ($FAB^+$) (m/z): Calcd for $C_{13}H_{15}{}^{35}Cl_2N_2O_2$ ($MH^+$): 301.0511, 303.0451, 305.0452. Found: 301.0520, 303.0478, 305.0444.

Example 14

Synthesis of 2-bromo-4,6-dichloromelatonin (12) from 4,6-dichloromelatonin (11)

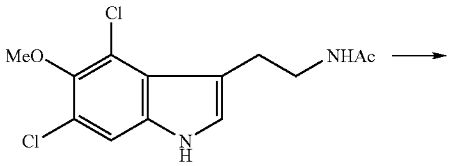

11

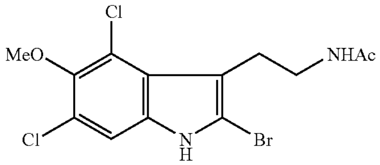

12

4,6-Dichloromelatonin (11) (6.2 mg, 0.021 mmol) was dissolved in 1.0 ml of a mixed solvent of chloroform/diethyl ether (1:1, v/v), 5.9 mg (0.018 mmol) of pyridinium bromide perbromide was added thereto, and the mixture was stirred at room temperature for 36 hours. Chloroform was added to the reaction solution, and the organic phase was washed with saturated saline and then dried over sodium sulfate, followed by removal of the solvent by distillation. The residue was subjected to thin-layer chromatography using silica gel as a carrier and a mixed solvent of chloroform/methanol (97:3, v/v) as a developing solvent, and a band with the Rf value of 0.36-0.28 was extracted with the use of chloroform/methanol (95:5, v/v). Thus, 2.0 mg (26%) of the target compound was obtained. A colorless prism crystal was obtained via recrystallization from ethyl acetate.

mp: 227° C. to 229° C. (decomposition)

IR (KBr): 3361, 1653 $cm^{-1}$ $^1$H-NMR ($CDCl_3$) δ: 1.93 (3H, s), 3.15 (2H, t, J=6.6 Hz), 3.58 (2H, q, J=6.6 Hz, changed into t, J=6.6 Hz via deuteration), 5.55 (1H, br s, eliminated via deuteration), 7.25 (1H, s), 8.28 (1H, br s, eliminated via deuteration)

High-resolution mass spectrometry (m/z): Calcd for $C_{13}H_{14}BrCl_2N_2O_2$ ($MH^+$): 378.9615, 380.9586, 380.9595, 382.9557, 382.9566, 384.9536. Found: 378.9614, 380.9565, 380.9565, 382.9547, 382.9547, 384.9557

Example 15

Test for Inspecting Influence of Indole Derivative on Bone Cell

In accordance with the method described in N. Suzuki and A. Hattori, J. Pineal Res., 33, 253-258, 2002, influences of an indole derivative on bone cells were inspected.

A female goldfish (body weight: about 30 g) was put under anesthesia with MS222 (ethyl 3-aminobenzoate, methane sulfonic acid salt) (Aldrich), and a desired number of scales were peeled off. The scales were washed twice in Eagle's minimum essential medium (ICN Biomedicals Inc.) comprising 1% antibiotics (a mixture of penicillin and streptomycin). Medium of the same type was introduced into each well of a 24-well plate in amounts of 1 ml, several scales were introduced to each well (8 scales in general), and $10^{-4}$, $10^{-6}$, and $10^{-8}$ M indole derivatives were applied to separate wells. Subsequently, the scales were cultured at 15° C. for 6 hours. Also, a group to which no indole derivative had been added was prepared (a control group), and influences thereof on osteoclasts and osteoblasts were compared. Two control groups, i.e., a group for inspecting osteoclasts and a group for inspecting osteoblasts, were provided. Specifically, a total of 8 wells were provided for the control and $10^{-4}$, $10^{-6}$, and $10^{-8}$ M indole derivatives (2 wells for each thereof). Accordingly, 3 types of indole derivatives can be inspected with the use of a 24-well plate.

After the culture, medium was removed, 0.05 M cacodylate buffer (pH 7.4) containing 10% formalin was added, and the scales were immobilized. The scales were stored in 0.05 M cacodylate buffer at 4° C. until the measurement of enzyme activity was initiated.

2-Bromomelatonin (a compound represented by formula (I) wherein X represents a bromine atom; $R^1$ represents a hydrogen atom; $R^2$ represents methyl; $R^3$, $R^5$ and $R^6$ each represent a hydrogen atom; and $R^4$ represents methyl), which was subjected to the test, was a known compound, and it was synthesized by the method described in M. Somei, Y. Fukui, M. Hasegawa, N. Oshikiri, and T. Hayashi, Heterocycles, 53, 1725-1736, 2000.

(1) Assay of Influences Imposed on Osteoclasts, i.e., Assay of Tartaric Acid-Resistant Acid Phosphatase (TRAP) Activity The immobilized scales were removed from the plate, and the weights thereof were measured. Thereafter, the scales were introduced into a 96-well microplate, 200 μl of 100 mM acetate buffer containing 20 mM tartaric acid and 10 mM paranitrophenol phosphate (substrate) was introduced to each well, reaction was allowed to proceed at 25° C. for 1 hour, and an aqueous solution of 2N sodium hydroxide (50 μl) was then added in order to terminate the reaction. The solution after the reaction (150 μl) was transferred to the other microplate, and the amount of paranitrophenol (pNP) generated by TRAP was measured using a spectrophotometer (405 nm). The osteoclast activity was indicated in terms of the amount of paranitrophenol phosphate decomposed and that of pNP produced within 1 hour per mg of the scales.

Figure 1B:
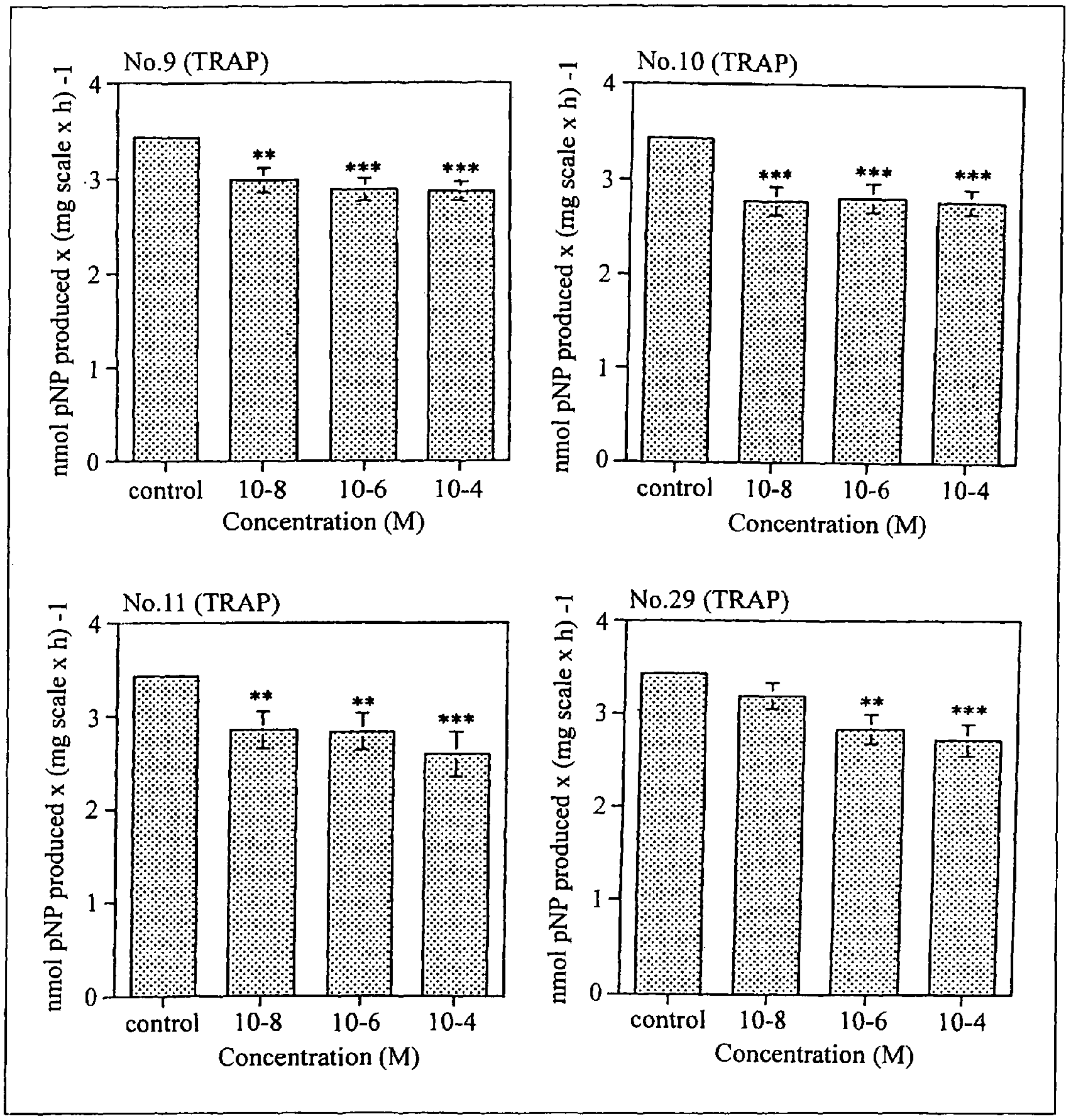
FIG. 1B shows influences of various indole derivatives on osteoclasts.

The results are shown in FIG. 1A, FIG. 1B, and Table 1.

TABLE 1

| TRAP activity | | |
|---|---|---|
| Indole derivatives | Concentration (M) | Amount of paranitrophenol produced (nmol/mg of scales/hr) |
| Melatonin | $10^{-8}$ | 2.91 ± 0.13*** |
| | $10^{-6}$ | 2.69 ± 0.15*** |
| | $10^{-4}$ | 2.67 ± 0.11*** |
| 2-Bromomelatonin | $10^{-8}$ | 3.02 ± 0.23 |
| | $10^{-6}$ | 2.62 ± 0.17** |
| | $10^{-4}$ | 2.83 ± 0.23* |
| 2,4,6-Tribromomelatonin | $10^{-8}$ | 2.88 ± 0.08** |
| | $10^{-6}$ | 2.87 ± 0.13** |
| | $10^{-4}$ | 2.93 ± 0.18** |
| 1-Allyl-2,4,6-tribromo-melatonin | $10^{-8}$ | 2.99 ± 0.13** |
| | $10^{-6}$ | 2.89 ± 0.12*** |
| | $10^{-4}$ | 2.87 ± 0.10*** |
| 2,4,6-Tribromo-1-propargylmelatonin | $10^{-8}$ | 2.78 ± 0.15*** |
| | $10^{-6}$ | 2.82 ± 0.15*** |
| | $10^{-4}$ | 2.78 ± 0.13*** |
| 1-Benzyl-2,4,6-tribromo-melatonin | $10^{-8}$ | 2.85 ± 0.20** |
| | $10^{-6}$ | 2.83 ± 0.20** |
| | $10^{-4}$ | 2.59 ± 0.24*** |
| 2,4,6,7-Tetrabromo-melatonin | $10^{-8}$ | 3.19 ± 0.14 |
| | $10^{-6}$ | 2.83 ± 0.16** |
| | $10^{-4}$ | 2.71 ± 0.17*** |
| Control | (Not added) | 3.43 ± 0.04 |

*$p < 0.05$
**$p < 0.01$
***$p < 0.001$ (2) Assay of Influences Imposed on Osteoblasts, i.e., Assay of Alkaline Phosphatase (ALP) Activity The immobilized scales were removed from the plate, and the weights thereof were measured. Thereafter, the scales were introduced into a 96-well microplate, 200 μl of 100 mM tris-HCl buffer (pH 9.5) comprising 10 mM paranitrophenol phosphate (substrate), 1 mM magnesium chloride, and 0.1 mM zinc chloride was introduced into each well, the reaction was allowed to proceed at 25° C. for 1 hour, and an aqueous solution of 2N sodium hydroxide (50 μl) was added thereto in order to terminate the reaction. Thereafter, 150 μl of the solution after the reaction was transferred to the other microplate, and the amount of pNP generated by ALP was measured using a spectrophotometer (405 nm) to determine the activity.

Figure 2A:
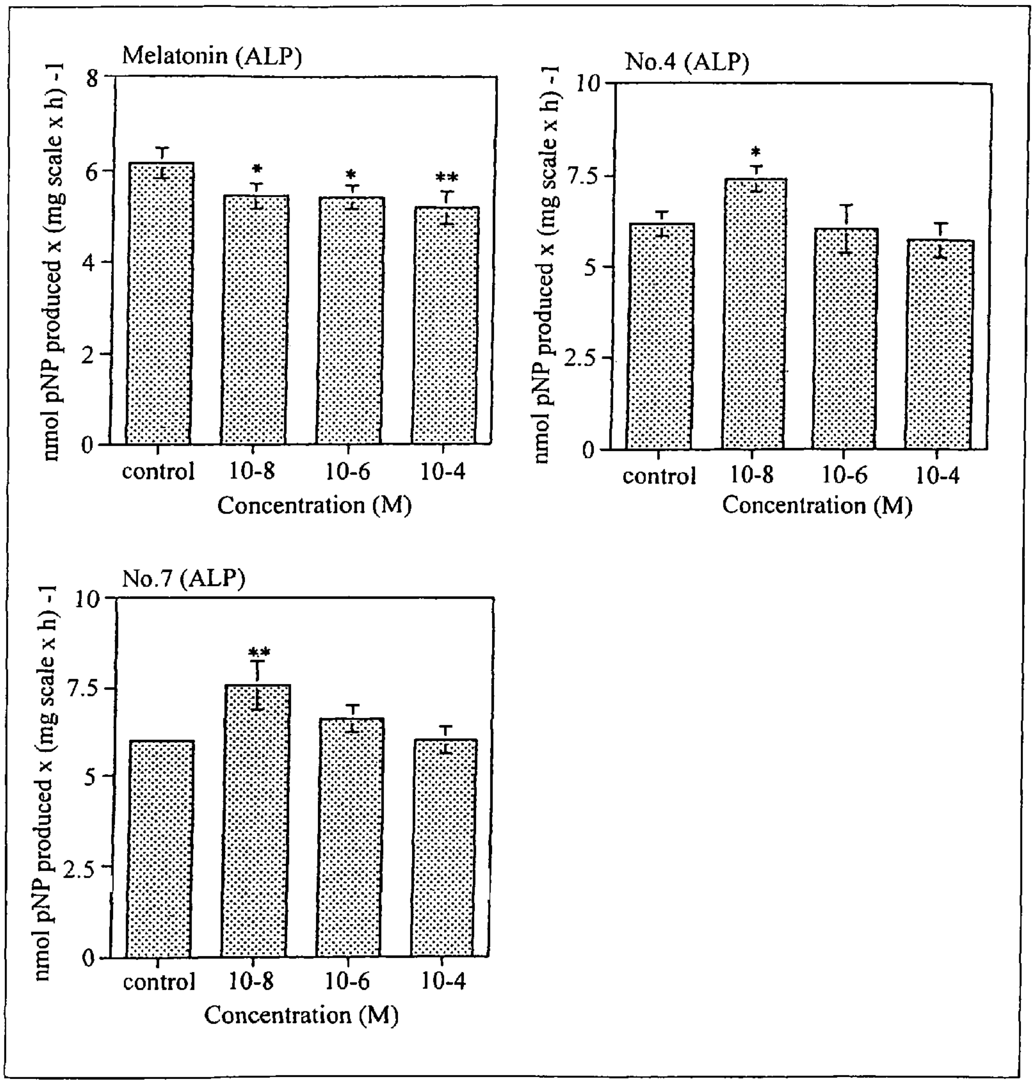
FIG. 2A shows influences of various indole derivatives on osteoblasts.
Figure 2B:
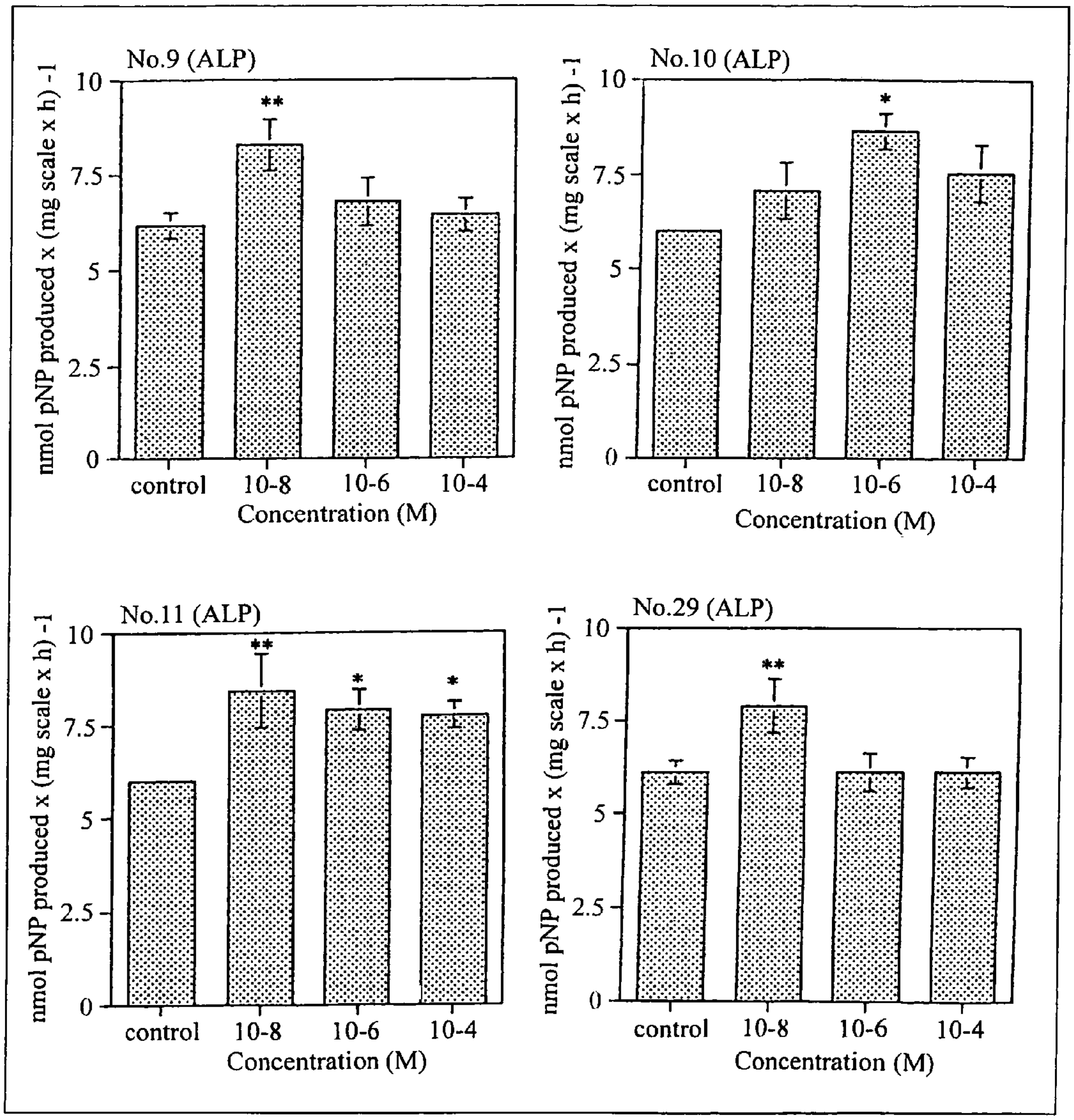
FIG. 2B shows influences of various indole derivatives on osteoblasts.

The results are shown in FIG. 2A, FIG. 2B, and Tables 2A to 2G.

TABLE 2A

| ALP activity | | |
|---|---|---|
| Indole derivative | Concentration (M) | Amount of paranitrophenol produced (nmol/mg of scales/hr) |
| Melatonin | $10^{-8}$ | 5.45 ± 0.27* |
| | $10^{-6}$ | 5.42 ± 0.25* |
| | $10^{-4}$ | 5.19 ± 0.36** |
| Control | (Not added) | 6.17 ± 0.34 |

*p < 0.05
**p < 0.01

TABLE 2B

| ALP activity | | |
|---|---|---|
| Indole derivative | Concentration (M) | Amount of paranitrophenol produced (nmol/mg of scales/hr) |
| 2-Bromomelatonin | $10^{-8}$ | 7.41 ± 0.35* |
| | $10^{-6}$ | 6.03 ± 0.66 |
| | $10^{-4}$ | 5.72 ± 0.47 |
| Control | (Not added) | 6.17 ± 0.34 |

*p < 0.05

TABLE 2C

| ALP activity | | |
|---|---|---|
| Indole derivative | Concentration (M) | Amount of paranitrophenol produced (nmol/mg of scales/hr) |
| 2,4,6-Tribromo-melatonin | $10^{-8}$ | 7.58 ± 0.70** |
| | $10^{-6}$ | 6.61 ± 0.38 |
| | $10^{-4}$ | 6.00 ± 0.38 |
| Control | (Not added) | 6.00 ± 0.13 |

**p < 0.01

TABLE 2D

| ALP activity | | |
|---|---|---|
| Indole derivative | Concentration (M) | Amount of paranitrophenol produced (nmol/mg of scales/hr) |
| 1-Allyl-2,4,6-tribromomelatonin | $10^{-8}$ | 8.30 ± 0.68** |
| | $10^{-6}$ | 6.79 ± 0.63 |
| | $10^{-4}$ | 6.44 ± 0.44 |
| Control | (Not added) | 6.17 ± 0.34 |

**p < 0.01

TABLE 2E

| ALP activity | | |
|---|---|---|
| Indole derivative | Concentration (M) | Amount of paranitrophenol produced (nmol/mg of scales/hr) |
| 2,4,6-Tribromo-1-propargylmelatonin | $10^{-8}$ | 7.07 ± 0.75 |
| | $10^{-6}$ | 8.66 ± 0.47* |
| | $10^{-4}$ | 7.55 ± 0.76 |
| Control | (Not added) | 6.00 ± 0.13 |

*p < 0.05

TABLE 2F

| ALP activity | | |
|---|---|---|
| Indole derivative | Concentration (M) | Amount of paranitrophenol produced (nmol/mg of scales/hr) |
| 1-Benzyl-2,4,6-tribromo-melatonin | $10^{-8}$ | 8.44 ± 1.00** |
| | $10^{-6}$ | 7.92 ± 0.55* |
| | $10^{-4}$ | 7.77 ± 0.37* |
| Control | (Not added) | 6.00 ± 0.13 |

*p < 0.05
**p < 0.01

TABLE 2G

| ALP activity | | |
|---|---|---|
| Indole derivative | Concentration (M) | Amount of paranitrophenol produced (nmol/mg of scales/hr) |
| 2,4,6,7-Tetrabromo-melatonin | $10^{-8}$ | 7.90 ± 0.73** |
| | $10^{-6}$ | 6.12 ± 0.50 |
| | $10^{-4}$ | 6.12 ± 0.41 |
| Control | (Not added) | 6.11 ± 0.31 |

**p < 0.01

As is apparent from FIG. 1A, FIG. 1B, Table 1, FIG. 2A, FIG. 2B, and Tables 2A to Table 2G, melatonin suppressively acts on osteoclasts and osteoblasts. In contrast, the indole derivative of the present invention suppresses osteoclasts but activates osteoblasts. Also, activity of the indole derivative of the present invention for suppressing osteoclasts was higher at high indole concentrations ($10^{-4}$M), and activity of activating osteoblasts was higher at low concentrations ($10^{-8}$M). This indicates that the indole derivative of the present invention can exhibit its effects at low concentrations and can serve as an excellent therapeutic agent for osteoporosis.

All publications, patents, and patent applications cited herein are incorporated herein by reference in their entirety.

INDUSTRIAL APPLICABILITY

The present invention is applicable to the pharmaceutical fields, such as for a therapeutic agent for osteoporosis, an osteoblast activator, and an osteoclast suppressor.

The invention claimed is:

1. A compound represented by formula (I') or a salt thereof:

(I')

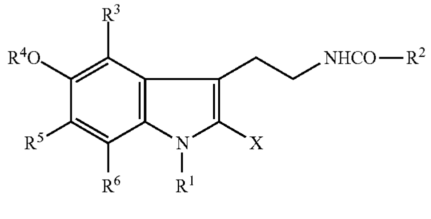

wherein:

X represents a bromine atom; $R^1$ represents a substituted or unsubstituted $C_{2-6}$ alkenyl, substituted or unsubstituted $C_{2-6}$ alkynyl, a substituted or unsubstituted aromatic group, substituted or unsubstituted aralkyl, substituted or unsubstituted arylsulfonyl, substituted or unsubstituted $C_{1-6}$ alkylsulfonyl, or hydroxyl; $R^2$ represents substituted or unsubstituted $C_{1-21}$ alkyl; $R^3$ and $R^5$ are the same or different and each represents a halogen atom; $R^6$ represents a hydrogen atom or a halogen atom; and $R^4$ represents a hydrogen atom or substituted or unsubstituted $C_{1-6}$ alkyl.

2. The compound represented by formula (I') according to claim 1 or a salt thereof, wherein $R^1$ represents substituted or unsubstituted $C_{2-6}$ alkenyl, substituted or unsubstituted $C_{2-6}$ alkynyl, a substituted or unsubstituted aromatic group, substituted or unsubstituted aralkyl, substituted or unsubstituted arylsulfonyl, or substituted or unsubstituted $C_{1-6}$ alkylsulfonyl; $R^2$ represents methyl; $R^3$ and $R^5$ each represents a bromine atom; $R^6$ represents a hydrogen atom or a bromine atom; and $R^4$ represents methyl.

3. A pharmaceutical composition comprising:

as an active ingredient, the compound according to claim 1 or a pharmaceutically acceptable salt thereof; and a pharmaceutically acceptable carrier.

4. The compound represented by formula (I') according to claim 1, wherein $R^3$ and $R^5$ each represents a bromine atom.

5. The compound represented by formula (I') according to claim 1, wherein $R^2$ is the $C_{2-21}$ alkyl and is selected from the group consisting of ethyl, propyl, isopropyl, butyl, isobutyl, sec-butyl, tert-butyl, pentyl, isopentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, cyclopropyl, cyclobutyl, cyclopentyl and cyclohexyl.

6. The compound represented by formula (I') according to claim 1 or a salt thereof, wherein $R^1$ represents substituted or unsubstituted $C_{2-6}$ alkenyl, substituted or unsubstituted $C_{2-6}$ alkynyl, or substituted or unsubstituted aralkyl; and $R^3$ and $R^5$ each represents a bromine atom.

7. The compound represented by formula (I') according to claim 1 or a salt thereof, wherein $R^1$ represents substituted or unsubstituted allyl, substituted or unsubstituted propargyl, substituted or unsubstituted benzyl, or substituted or unsubstituted phenethyl; and $R^3$ and $R^5$ each represents a bromine atom.

8. The compound represented by formula (I') according to claim 1 or a salt thereof, wherein $R^1$ represents allyl, propargyl, benzyl, or phenethyl; and $R^3$ and $R^5$ each represents a bromine atom.

9. The compound represented by formula (I') according to claim 1 or a salt thereof, wherein $R^1$ represents substituted or unsubstituted aralkyl; and $R^3$ and $R^5$ each represents a bromine atom.

10. The compound represented by formula (I') according to claim 1 or a salt thereof, wherein $R^1$ represents substituted or unsubstituted benzyl, or substituted or unsubstituted phenethyl; and $R^3$ and $R^5$ each represents a bromine atom.

11. The compound represented by formula (I') according to claim 1 or a salt thereof, wherein $R^1$ represents benzyl, or phenethyl; and $R^3$ and $R^5$ each represents a bromine atom.

12. The compound represented by formula (I') according to claim 1 or a salt thereof, wherein $R^6$ represents a bromine atom.

* * * * *